United States Patent [19]
Shirai et al.

[11] Patent Number: 5,763,601
[45] Date of Patent: Jun. 9, 1998

[54] NAPHTHALOCYANINE COMPOUNDS, NAPHTHALOCYANINE POLYMERS AND METHOD FOR MAKING

[75] Inventors: Hirofusa Shirai, 2496, Nagase, Maruko-cho, Chiisagata-gun, Nagano; Mutsumi Kimura, Ueda; Yuichi Kubota, Chiba, all of Japan

[73] Assignees: Hirofusa Shirai, Nagano; TDK Corporation, Tokyo, both of Japan

[21] Appl. No.: 806,156

[22] Filed: Feb. 25, 1997

Related U.S. Application Data

[62] Division of Ser. No. 326,918, Oct. 21, 1994, Pat. No. 5,633,370.

[30] Foreign Application Priority Data

Oct. 22, 1993 [JP] Japan ................................. 5-287483

[51] Int. Cl.$^6$ .......................... C07D 487/22; C09B 47/04
[52] U.S. Cl. ...................... 540/122; 252/600; 540/143
[58] Field of Search ................................. 540/122, 143

[56] References Cited

U.S. PATENT DOCUMENTS

| 4,663,084 | 5/1987 | Shirai et al. |  |
|---|---|---|---|
| 5,516,900 | 5/1996 | Kimura et al. |  |
| 5,618,930 | 4/1997 | Kimura et al. | 540/143 |
| 5,633,370 | 5/1997 | Shirai et al. | 540/122 |

*Primary Examiner*—Mukund J. Shah
*Assistant Examiner*—Pavanaram K. Sripada
*Attorney, Agent, or Firm*—Oblon, Spivak, McClelland, Maier & Neustadt, P.C.

[57] ABSTRACT

Novel naphthalocyanine compounds are provided including nitro- and amino-substituted naphthalocyanine compounds, and vinyl-containing naphthalocyanine compounds. The compounds have improved solubility and high purity and are expected to find use as photo-functional materials such as dyes. Polymers are obtained using the vinyl-containing naphthalocyanine compounds. The polymers also have improved solubility, high purity, a high naphthalocyanine content and ease of control of the orientation of naphthalocyanine rings and are expected of use as various functional materials.

4 Claims, 1 Drawing Sheet

NAPHTHALOCYANINE COMPOUNDS, NAPHTHALOCYANINE POLYMERS AND METHOD FOR MAKING

This is a Division of application Ser. No. 08/326,918 filed on Oct. 21, 1994, allowed now Patented U.S. Pat. No. 5,633,370.

BACKGROUND OF THE INVENTION

This invention relates to novel naphkthalocyanine compounds and a method for preparing the same. More particularly, it relates to nitro-substituted naphthalocyanine compounds, amino-substituted naphthalocyanine compounds, vinyl-containing naphthalocyanine compounds, and methods for preparing them. It also relates to a novel naphthalocyanine polymer obtained by starting with the novel vinyl-containing naphthalocyanine compound and a method for preparing the same.

Phthalocyanines and naphthalocyanines which are derivatives thereof are macrocyclic dyes having a structure similar to porphyrin compounds and they are stable against light, heat and moisture, chemically stable and fast. Especially metal phthalocyanines have been widely used as dyes or pigments because of their high stability and definite color tone. They now draw interest as materials for light absorption, electric conduction, photo-conduction, energy conversion, electrode and catalyst because of the presence of a metal ion in a large π-electron conjugated system. However, they are essentially difficult to dissolve, to work up to high purity, and to handle under ambient conditions.

Attempts were made to produce a polymer having carried thereon a phthalocyanine, especially a metal phthalocyanine for facilitating formation of films or similar items capable of exerting a high function. Such a metal phthalocyanine-containing polymer is produced, for example, by synthesizing a metal phthalocyanine derivative having a reactive group and reacting it with a polymer having introduced therein a group reactive with the reactive group. See D. Wohrle et al., J. Org. Organomet. Polym., 1, 1, 115 (1991). This type of synthetic method wherein a metal phthalocyanine derivative is reacted with a polymer, however, suffers from the problem that the reaction product has an inconsistent content of metal phthalocyanine ring.

Also proposed were metal phthalocyanine derivatives which have a vinyl group and are thus polymerizable by themselves as disclosed in Japanese Patent Application Kokai (JP-A) Nos. 178672/1985 and 53990/1987. It was also attempted to produce polymers by starting with them as disclosed in JP-A 50311/1987. The metal phthalocyanine derivatives are obtained by starting with a metal phthalocyanine tetracarboxylic acid and introducing a vinyl group therein. Synthesis of a metal phthalocyanine tetracarboxylic acid entails formation of much by-products probably because of solid-phase reaction. Also most intermediates to the vinyl group-containing metal phthalocyanine derivatives are sparingly soluble and difficult to purify. Then the final products are low in purity. While vinyl groups are introduced in a number proportional to the number of carboxy groups and thus typically four vinyl groups are introduced, often those products having vinyl groups in a number other than the desired number are concomitantly produced, which are difficult to separate and thus cause a lowering of purity. Moreover, the vinyl group-containing metal phthalocyanine derivatives are less soluble.

The resulting polymer is often a three-dimensional polymer since the metal phthalocyanine derivative has four vinyl groups as a general rule. This complies with the purpose of having a vinyl polymer carry a metal phthalocyanine like a crosslinking agent, but not with the purpose of synthesizing a linear polymer.

The problems discussed above also apply to naphthalocyanine compounds.

It is thus desired to develop a polymerizable naphthalocyanine compound having improved solubility and purity and offering a freedom of choice of a ligand metal to the naphthalocyanine. It is also desired to produce a polymer from the naphthalocyanine compound as a starting monomer, the polymer having improved solubility, high purity, easy control of orientation, and a high naphthalocyanine content.

SUMMARY OF THE INVENTION

A first object of the present invention is to provide a novel naphthalocyanine compound and nitro- and amino-substituted naphthalocyanine compound which have improved solubility and high purity and which are expected to find use as a photo-functional material as well as a method for preparing the same.

A second object of the present invention is to provide a novel vinyl-containing naphthalocyanine compound having improved solubility and high purity, containing a polymerizable vinyl group within its molecule and expected to find use as a photo-functional material as well as a method for preparing the same.

A third object of the present invention is to provide a novel naphthalocyanine polymer having a high naphthalocyanine content, easy control of orientation, improved solubility, and high purity, and expected to find use as a photo-functional material as well as a method for preparing the same using the vinyl-containing naphthalocyanine compound.

In a first aspect, the present invention provides a naphthalocyanine compound of the following general formula (1):

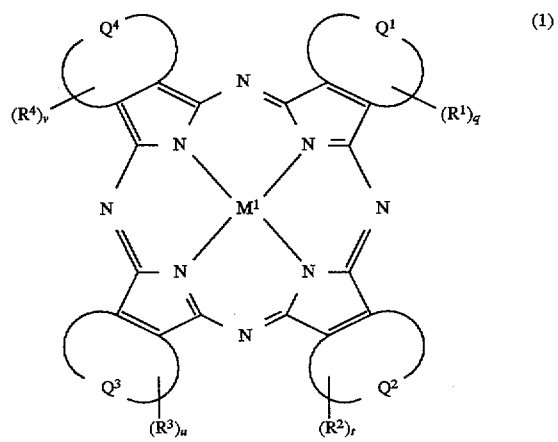

wherein each of $Q^1$, $Q^2$, $Q^3$, and $Q^4$ is a group of atoms to form a benzene ring or naphthalene ring fused to the adjacent pyrrole ring, at least one of the rings formed by $Q^1$, $Q^2$, $Q^3$, and $Q^4$ being a naphthalene ring, each of $R^1$, $R^{2}$, $R^3$, and $R^4$, which may be identical or different, is a monovalent substituent, letter q is 0 or an integer of 1 to 4 when $Q^1$ forms a benzene ring, or 0 or an integer of 1 to 6 when $Q^1$ forms a naphthalene ring, t is 0 or an integer of 1 to 4 when $Q^2$ forms a benzene ring, or 0 or an integer of 1 to 6 when $Q^2$ forms a naphthalene ring, u is 0 or an integer of 1 to 4 when $Q^3$ forms a benzene ring, or 0 or an integer of 1 to 6 when $Q^3$ forms a naphthalene ring, v is 0 or an integer of 1 to 4 when $Q^4$ forms a benzene ring, or 0 or an integer of 1 to 6 when $Q^4$ forms a naphthalene ring, with the proviso that q, t, u and v are not equal to 0 at the same time and the sum of q+t+u+v is an integer of at least 1, where q, t, u, and v are more than one, the corresponding $R^1$, $R^2$, $R^3$, and $R^4$ groups may be identical or different, and $M^1$ is a center atom.

In a second aspect, the invention also provides a nitro-substituted naphthalocyanine compound of the following general formula (2):

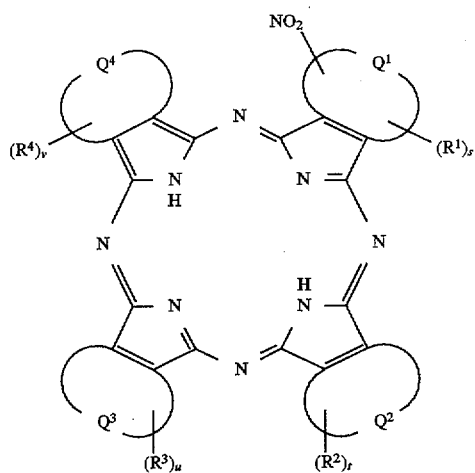

(2)

wherein $Q^1$ to $Q^4$ and $R^1$ to $R^4$ are as defined above, letter s is 0 or an integer of 1 to 3 when $Q^1$ forms a benzene ring, or 0 or an integer of 1 to 5 when $Q^1$ forms a naphthalene ring, letters t, u and v are as defined above, with the proviso that s, t, u and v are not equal to 0 at the same time and the sum of s+t+u+v is an integer of at least 1, where s, t, u, and v are more than one, the corresponding $R^1$, $R^2$, $R^3$, and $R^4$ groups may be identical or different.

The two hydrogen atoms positioned centrally of the nitro-substituted naphthalocyanine compound may be replaced by a metal.

In a third aspect, the invention provides an amino-substituted naphthalocyanine compound of the following general formula (3):

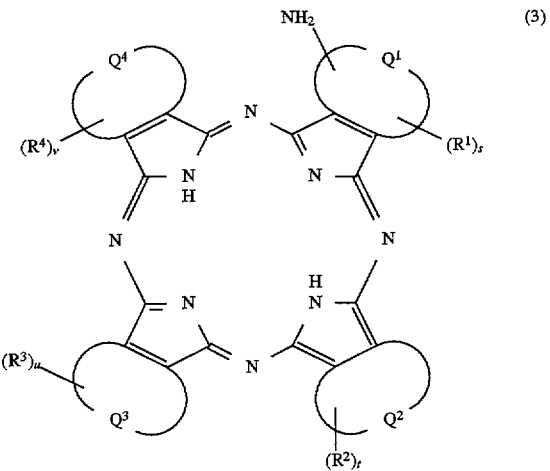

(3)

wherein $Q^1$ to $Q^4$, $R^1$ to $R^4$, s, t, u and v are as defined above.

The two hydrogen atoms positioned centrally of the amino-substituted naphthalocyanine compound may be replaced by a metal.

In a fourth aspect, the invention provides a vinyl-containing naphthalocyanine compound of the following general formula (4):

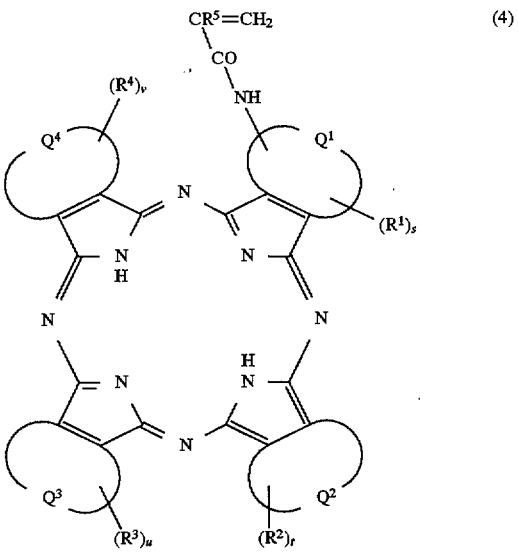

(4)

wherein $Q^1$ to $Q^4$, $R^1$ to $R^4$, s, t, u and v are as defined above, and $R^5$ is a hydrogen atom or an alkyl group.

The two hydrogen atoms positioned centrally of the vinyl-containing naphthalocyanine compound may be replaced by a metal.

The naphthalocyanine compound of formula (1) can be prepared by reacting a phthalonitrile compound system including at least one dicyanonaphthalene which may be replaced by $R^1$, $R^2$, $R^3$ or $R^4$ and optionally, at least one phthalonitrile which may be replaced by $R^1$, $R^2$, $R^3$ or $R^4$.

The nadhthalocyanine compound of formula (4) can be prepared by reacting a phthalonitrile compound system including at least one of a phthalonitrile which may be replaced by $R^2$, $R^3$ or $R^4$ and a dicyanonaphthalene which may be replaced by $R^2$, $R^3$ or $R^4$ and at least one of a nitrophthalonitrile which may be replaced by $R^1$ and a dicyanonitronaphthalene which may be replaced by $R^1$, thereby forming a nitro-substituted naphthalo-cyanine compound of formula (2); reducing the nitro group of said nitro-substituted naphthalocyanine compound into an amino-substituted naphthalocyanine compound of formula (3); and introducing an acryloyl group into the amino group of said amino-substituted naphthalocyanine compound to form a naphthalocyanine compound of formula (4).

In a fifth aspect, the invention provides a naphthalocyanine polymer having a structural unit of the following general formula (5):

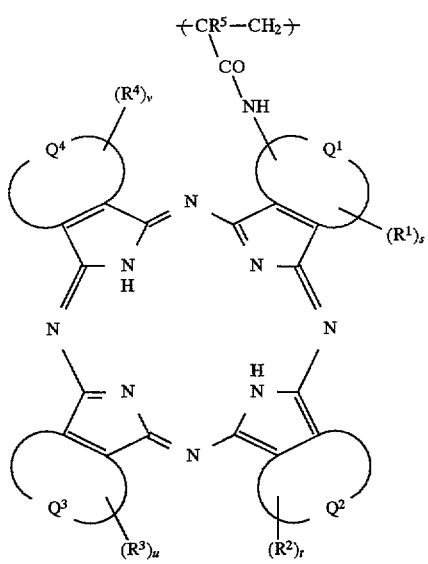

wherein $Q^1$ to $Q^4$, $R^1$ to $R^4$, s, t, u, v, and $R^5$ are as defined above.

In a sixth aspect, the invention provides a naphthalocyanine polymer having a structural unit of the following general formula (6):

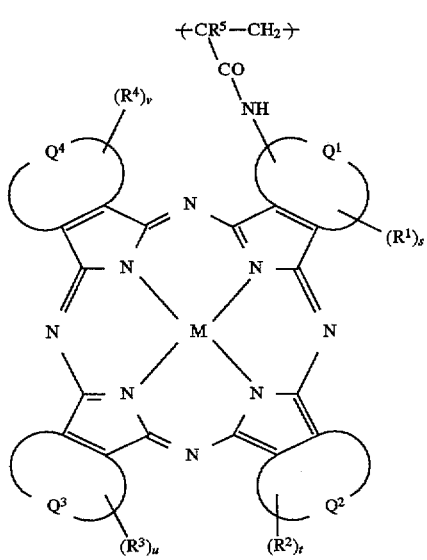

wherein $Q^1$ to $Q^4$, $R^1$ to $R^4$ s, t, u, v, and $R^5$ are as defined above, and M is a metal atom.

The naphthalocyanine polymer of formula (5) is prepared by polymerizing a naphthalocyanine compound of formula (4). The naphthalocyanine polymer of formula (6) is prepared by substituting a metal for the two hydrogen atoms positioned centrally of the naphthalocyanine ring of a naphthalocyanine polymer of formula (5).

DETAILED DESCRIPTION OF THE INVENTION

Compound

Figure 1:
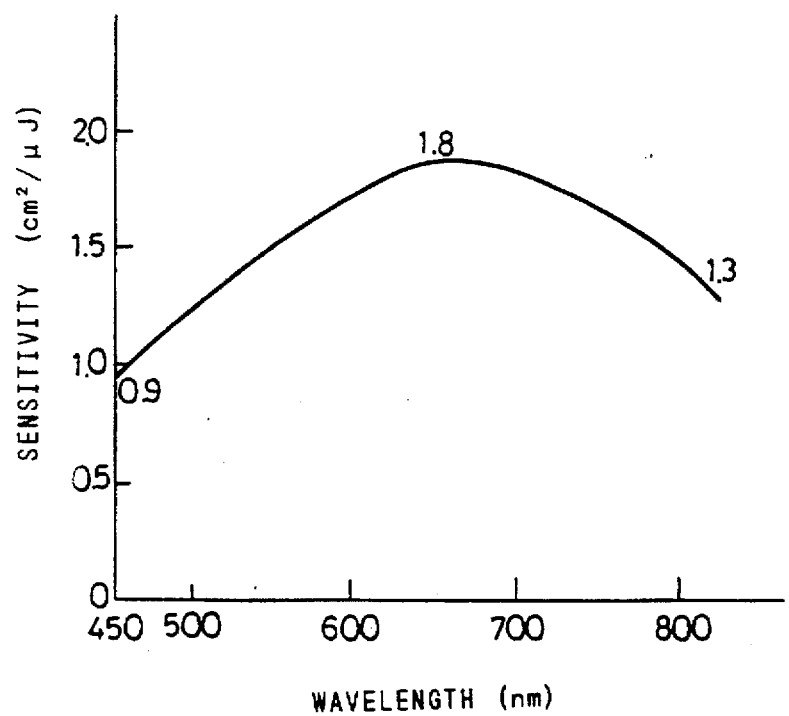
FIG. 1 is a graph showing the sensitivity of a photosensitive member of Example 24 as a function of wavelength.

The present invention provides naphthalocyanine compounds of formula (1).

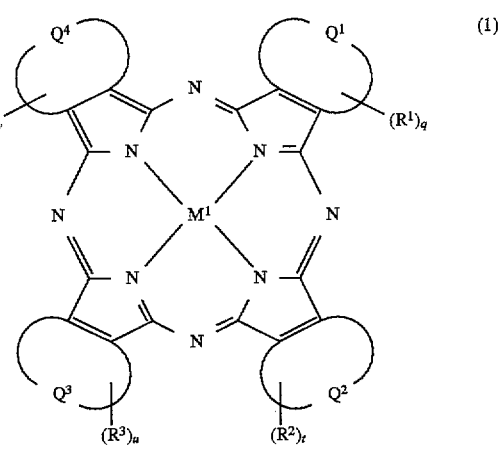

In formula (1), each of $Q^1$, $Q^2$, $Q^3$, and $Q^4$ is a group of atoms necessary to form a benzene ring or naphthalene ring fused to the adjacent pyrrole ring. At least one of the rings formed by $Q^1$, $Q^2$, $Q^3$, and $Q^4$ is a naphthalene ring.

$R^1$, $R^2$, $R^3$, and $R^4$ are independently selected from monovalent substituents and they may be identical or different. They are attached to the benzene or naphthalene ring formed by $Q^1$, $Q^2$, $Q^3$, and $Q^4$. Examples of the monovalent substituent represented by $R^1$, $R^2$, $R^3$, and $R^4$ include nitro, amino, alkyl and alkoxy groups and vinyl-containing groups.

The alkyl groups represented by $R^1$, $R^2$, $R^3$, and $R^4$ may be straight or branched and substituted or unsubstituted. When substituted, exemplary substituents are halogen atoms such as F and Cl. Alkyl groups having 2 to 6 carbon atoms are preferred. Among others, ethyl, propyl, butyl and hexyl groups are more preferred, with t-butyl, s-butyl, t-pentyl, t-hexyl and i-propyl groups being especially preferred. Also preferred are such alkyl groups substituted with halogen atoms such as fluorine atoms, for example, $C_2F_5$- and $t$-$C_4F_9$-.

The alkoxy groups represented by $R^1$, $R^2$, $R^3$, and $R^4$ are preferably those groups whose alkyl moiety has 2 to 6 carbon atoms as mentioned above. Ethoxy, propoxy, butoxy, pentyloxy, and hexyloxy groups are preferred, with t-butoxy, s-butoxy, t-pentyloxy t-hexyloxy and i-propoxy groups being especially preferred. Also preferred are such alkoxy groups substituted with halogen atoms such as fluorine atoms, for example, —OCH(F)($CH_3$).

The vinyl-containing groups represented by $R^1$, $R^2$, $R^3$, and $R^4$ are preferably acryloylamino and methacryloylamino groups.

Letter q is 0 or an integer of 1 to 4 when $Q^1$ forms a benzene ring, or 0 or an integer of 1 to 6 when $Q^1$ forms a naphthalene ring; t is 0 or an integer of 1 to 4 when $Q^2$ forms a benzene ring, or 0 or an integer of 1 to 6 when $Q^2$ forms a naphthalene ring; u is 0 or an integer of 1 to 4 when $Q^3$ forms a benzene ring, or 0 or an integer of 1 to 6 when $Q^3$ forms a naphthalene ring; v is 0 or an integer of 1 to 4 when $Q^4$ forms a benzene ring, or 0 or an integer of 1 to 6 when $Q^4$ forms a naphthalene ring. Where q, t, u, and v are 2 or more, the corresponding, $R^2$, $R^3$, and 4 groups may be identical or different. Note that all of q, t, u and v are not equal to 0 at the same time. The sum of q+t+u+v is an integer of at least 1, that is, an integer of 1 to 24, preferably an integer of 1 to 8.

$M^1$ is a center atom, for example, a pair of hydrogen atoms as found in formula (2) or a metal atom M which will be described later.

The naphthalocyanine compounds of formula (1) may be those of the following formula (7).

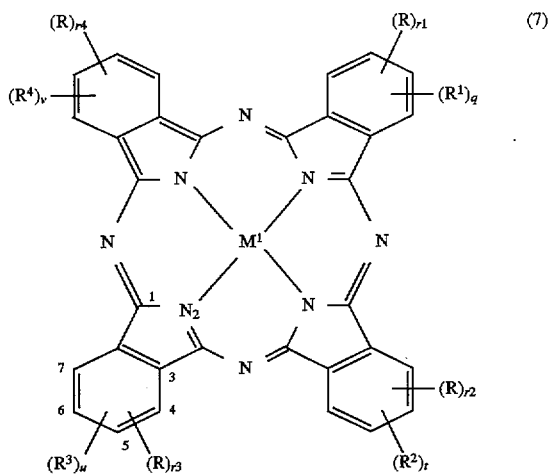

In formula (7), $R^1$ to $R^4$ are as defined in formula (1). Each of r1, r2, r3 and r4 is 0 or 2, with at least one of r1, r2, r3 and r4 being equal to 2. When r1, r2, r3 or r4 is 2, R's are monovalent substituents which are disposed adjacent to each other and attached together to form a fused benzene ring, for example, alkyl groups (e.g., methyl and ethyl) and alkenyl groups (e.g., vinyl and allyl). The fused benzene ring is fused to the isoindole ring at its 4, 5-positions, 5, 6-positions or 6, 7-positions, preferably at its 5, 6-positions though not limited thereto.

q, t, u, and v are 0 or an integer of 1 to 4 when corresponding r1, r2, r3 or r4 is equal to 0, or 0 or an integer of 1 to 6 when corresponding r1, r2, r3 or r4 is equal to 2. q, t, u and v are essentially as defined in formula (1).

Preferably, at least one of $R^1$ to $R^4$ attached to the benzene or naphthalene rings of the naphthalocyanine ring is an alkyl group having 2 to 6 carbon atoms or an alkoxy group having 2 to 6 carbon atoms.

The groups attached to the benzene or naphthalene ring other than the $C_2$-$C_6$ alkyl and $C_2$-$C_6$ alkoxy groups are preferably hydrogen atoms although in some cases, other alkyl groups such as methyl, other alkoxy groups such as methoxy or other substituent groups can be attached to the benzene or naphthalene ring.

Among the naphthalocyanine compounds of formula (1), exemplary preferred compounds are represented by the following formula (8). It should be noted that those naphthalocyanine compounds having a nitro group, amino group or vinyl-containing group as a substituent will be described later.

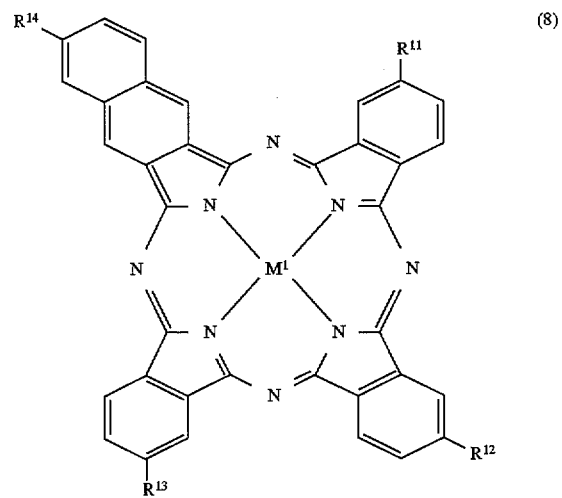

In formula (8), each of $R^{11}$, $R^{12}$, $R^{13}$, and $R^{14}$ is a hydrogen atom or an alkyl or alkoxy group as defined for $R^1$ to $R^4$ in formula (1). At least one of $R^{11}$, $R^{12}$, $R^{13}$ and $R^{14}$ is an alkyl or alkoxy group.

Preferred examples of the naphthalocyanine compounds of formula (1) are those of formula (8) wherein (8-1) $R^{11}=R^{12}=R^{13}=R^{14}=$t—$C_4H_9$—,
(8-2) $R^{11}=R^{12}=R^{13}=R^{14}=$t—$C_4H_9$—,
(8-3) $R^{11}=R^{12}=R^{13}=R^{14}=C_2F_5$—, and
(8-4) $R^{11}=R^{12}=R^{13}=R^{14}=$—OCH(F) (CH$_3$)

Also preferably $M^1$ is 2H or Si(OR$_1$)$_2$ as will be described later.

In formula (8), the four rings completed by $Q^1$, $Q^2$, $Q^3$, and $Q^4$ in formula (1) are three benzene rings and one naphthalene ring although the combination is not limited thereto. For the four rings combined, a choice may be made among zero to three benzene rings and one to four naphthalene rings. It is also understood that the number of substituents attached to the benzene and naphthalene rings is four in formula (8) although there can be attached six or eight substituents.

In the second aspect, the present invention provides nitro-substituted naphthalocyanine compounds of formula (2).

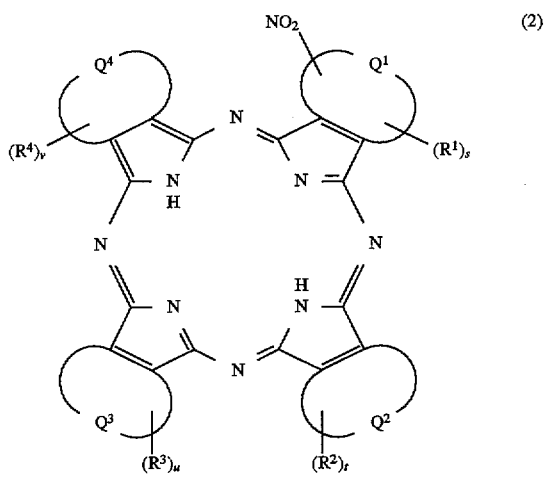

In formula (2), $Q^1$, $Q^2$, $Q^3$, and $Q^4$ are as defined in formula (1).

$R^1$, $R^2$, $R^3$, and $R^4$ are independently selected from monovalent substituents and they may be identical or different. They are attached to the benzene or naphthalene ring formed by $Q^1$, $Q^2$, $Q^3$, and $Q^4$. Exemplary monovalent substituents represented by $R^1$, $R^2$, $R^3$, and $R^4$ are alkyl and alkoxy groups as described for formula (1).

Letter s is 0 or an integer of 1 to 3 when $Q^1$ forms a benzene ring, or 0 or an integer of 1 to 5 when $Q^1$ forms a naphthalene ring; t is 0 or an integer of 1 to 4 when $Q^2$ forms a benzene ring, or 0 or an integer of 1 to 6 when $Q^2$ forms a naphthalene ring; u is 0 or an integer of 1 to 4 when $Q^3$ forms a benzene ring, or 0 or an integer of 1 to 6 when $Q^3$ forms a naphthalene ring; v is 0 or an integer of 1 to 4 when $Q^4$ forms a benzene ring, or 0 or an integer of 1 to 6 when $Q^4$ forms a naphthalene ring. Where s, t, u, and v are 2 or more, the corresponding $R^1$, $R^2$, $R^3$, and $R^4$ groups may be identical or different. Note that all of s, t, u and v are not equal to 0 at the same time. The sum of s+t+u+v is an integer of at least 1, that is, an integer of 1 to 23, preferably an integer of 1 to 8.

The nitro-substituted naphthalocyanine compounds of formula (2) may be those of the following formula (9).

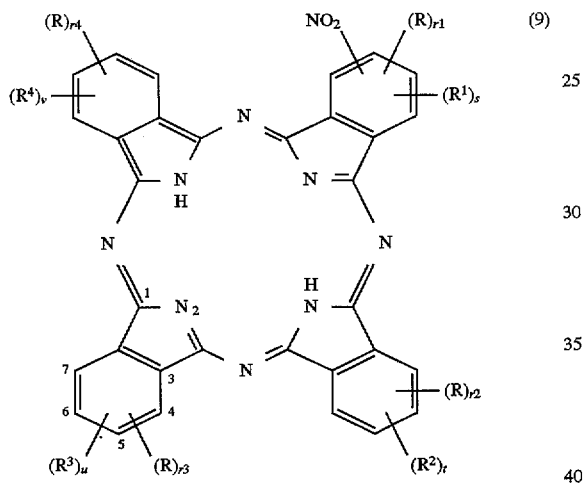

In formula (9), $R^1$ to $R^4$ are as defined in formula (1). Each of r1, r2, r3 and r4 is 0 or 2, with at least one of r1, r2, r3 and r4 being equal to 2. When r1, r2, r3 or r4 is 2, R's are monovalent substituents which are disposed adjacent to each other and attached together to form a fused benzene ring, for example, alkyl groups (e.g., methyl and ethyl) and alkenyl groups (e.g., vinyl and allyl). The fused benzene ring is fused to the isoindole ring at its 4, 5-positions, 5, 6-positions, or 6, 7-positions, preferably at its 5, 6-positions though not limited thereto.

Letter s is 0 or an integer of 1 to 3 when r1=0, or 0 or an integer of 1 to 5 when r1=2. t, u, and v are 0 or an integer of 1 to 4 when corresponding r2, r3 or r4 is equal to 0, or 0 or an integer of 1 to 6 when corresponding r2, r3 or r4 is equal to 2. t, u and v are essentially as defined in formula (2).

Preferably, at least one of $R^1$ to $R^4$, especially $R^2$ to $R^4$ attached to the benzene or naphthalene rings of the naphthalocyanine ring is an alkyl group having 2 to 6 carbon atoms or an alkoxy group having 2 to 6 carbon atoms. More preferably, s is equal to 0, t, u and v are equal to 1, and $R^2$, $R^3$ and $R^4$ are $C_2$-$C_6$ alkyl or $C_2$-$C_6$ alkoxy groups. In these preferred embodiments, the groups attached to the benzene or naphthalene ring other than the $C_2$-$C_6$ alkyl and $C_2$-$C_6$ alkoxy groups are preferably hydrogen atoms although in some cases, other alkyl groups such as methyl, other alkoxy groups such as methoxy or other substituent groups can be attached to the benzene or naphthalene ring.

Among the nitro-substituted naphthalocyanine compounds of formula (2), exemplary preferred compounds are represented by the following formulae (10) and (11).

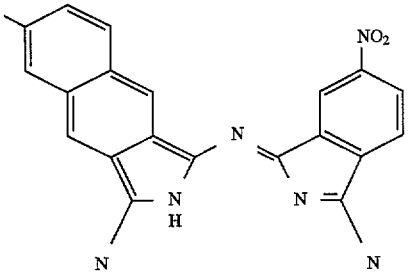

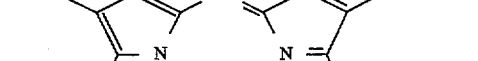

In formulae (10) and (11), each of $R^{12}$, $R^{13}$, $R_{14}$, is a hydrogen atom or an alkyl or alkoxy group as defined for $R^1$ to $R^4$ in formula (1). At least one of $R^{12}$, $R^{13}$, and $R^{14}$ is an alkyl or alkoxy group.

Preferred illustrative examples of the nitro-substituted naphthalocyanine compounds of formula (2) are shown in Table 1 which represents combinations of $R^{12}$, $R^{13}$, and $R^{14}$ in formulae (10) and (11).

TABLE 1

| Compound designation | $R^{12}$ | $R^{13}$ | $R^{14}$ |
|---|---|---|---|
| N-1 | t-$C_4H_9$ | t-$C_4H_9$ | t-$C_4H_9$ |
| N-2 | s-$C_4H_9$ | s-$C_4H_9$ | s-$C_4H_9$ |
| N-3 | t-$C_5H_{11}$ | t-$C_5H_{11}$ | t-$C_5H_{11}$ |
| N-4 | t-$C_6H_{13}$ | t-$C_6H_{13}$ | t-$C_6H_{13}$ |
| N-5 | i-$C_3H_7$ | i-$C_3H_7$ | i-$C_3H_7$ |

TABLE 1-continued

| Compound designation | $R^{12}$ | $R^{13}$ | $R^{14}$ |
|---|---|---|---|
| N-6 | t-$C_4H_9O$ | t-$C_4H_9O$ | t-$C_4H_9O$ |
| N-7 | s-$C_4H_9O$ | s-$C_4H_9O$ | s-$C_4H_9O$ |
| N-8 | t-$C_5H_{11}O$ | t-$C_5H_{11}O$ | t-$C_5H_{11}O$ |
| N-9 | t-$C_6H_{13}O$ | t-$C_6H_{13}O$ | t-$C_6H_{13}O$ |
| N-10 | i-$C_3H_7O$ | i-$C_3H_7O$ | i-$C_3H_7O$ |
| N-11 | $C_2F_5$ | $C_2F_5$ | $C_2F_5$ |
| N-12 | t-$C_4F_9$ | t-$C_4F_9$ | t-$C_4F_9$ |
| N-13 | $CH_3$>CHO F | $CH_3$>CHO F | $CH_3$>CHO F |

In formulae (10) and (11), the four rings completed by $Q^1$, $Q^2$, $Q^3$, and $Q^4$ in formula (1) are four naphthalene rings or three naphthalene rings combined with one benzene ring although the combination is not limited thereto. Any desired combination of the four rings may be used as previously described for formula (1). It is also understood that the number of substituents is not limited to four and there can be attached six or eight substituents.

The nitro-substituted naphthalocyanine compounds of the invention may be metal naphthalocyanine compounds wherein a metal substitutes for the two hydrogen atoms positioned centrally thereof.

The metal atom M used herein includes metal atoms belonging to Groups 1 to 14 (Groups 1A to 7A, 8, and 1B to 4B) in the Periodic Table. Examples are Li, Na, K, Mg, Ca, Ba, Ti, Zr, V, Nb, Ta, Cr, Mo, W, Mn, Tc, Fe, Co, Ni, Ru, Rh, Pd, Os, Ir, Pt, Cu, Ag, Au, Zn, Cd, Hg, Al, In, Tl, Si, Ge, Sn, and Pb. Among these, Li, Ti, V, Cr, Mn, Fe, Co, Ni, Cu, Zn, Al, and Si are preferred, Fe, Co, Ni, Cu, Zn, Al and Si are more preferred. It will be understood that V and Ti can coordinate in the form of VO and TiO, respectively, and one or two other ligands may coordinate to the metal atom from above or below. For silicon, for instance, it is introduced in the form of $Si(OH)_2$, which is converted into $Si(OR_1)_2$ wherein $R_1$ is an alkyl group whereby the introduction of the alkoxy groups above and below the silicon atom improves solubility.

Preferred among the metal naphthalocyanine compounds are those having the combination of $R^{12}$, $R^{13}$, and $R^{14}$ shown in Table 1 wherein the two hydrogen atoms are replaced by Fe, Co, Ni, Cu, and Zn, especially by Co, Cu, and Zn.

In the third aspect, the present invention provides amino-substituted naphthalocyanine compounds of formula (3):

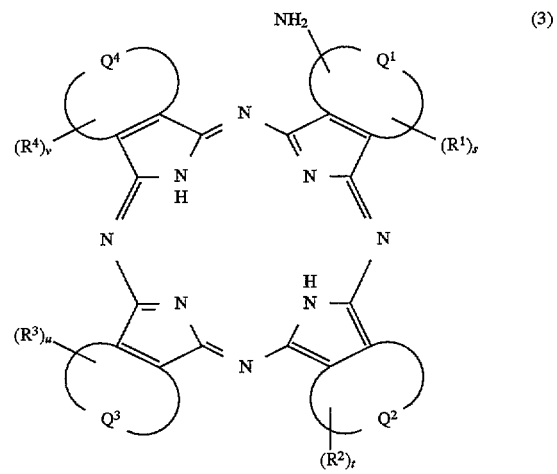
(3)

wherein $Q^1$ to $Q^4$, $R^1$ to $R^4$, s, t, u and v are as defined in formula (2).

The amino-substituted naphthalocyanine compounds of formula (3) may be those of the following formula (12):

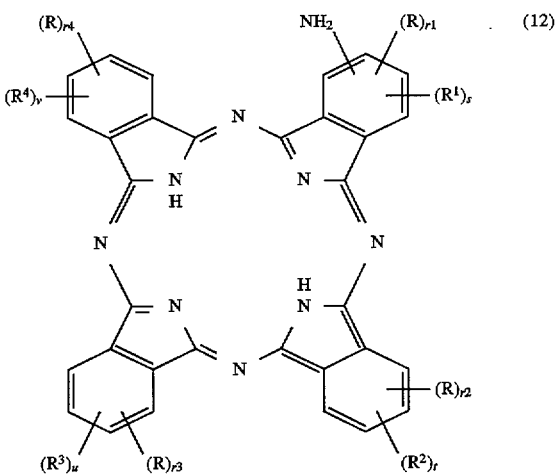
(12)

wherein R, r1 to r4, $R^1$ to $R^4$, s, t, u and v are as defined in formula (9) both for general and preferred examples.

Among the amino-substituted naphthalocyanine compounds of formula (3), exemplary preferred compounds are represented by the following formulae (13) and (14).

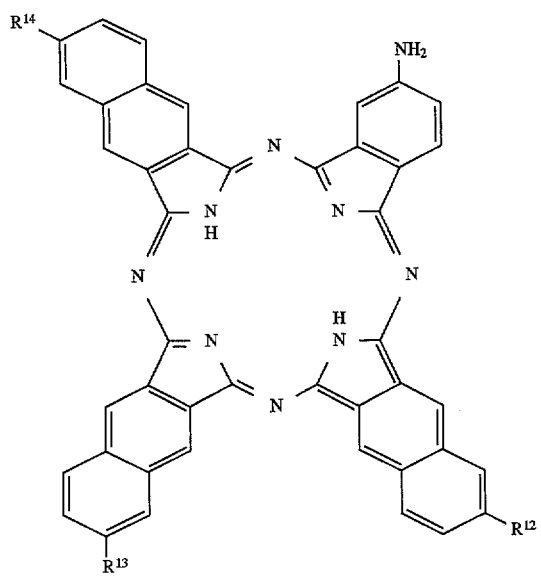

(13)

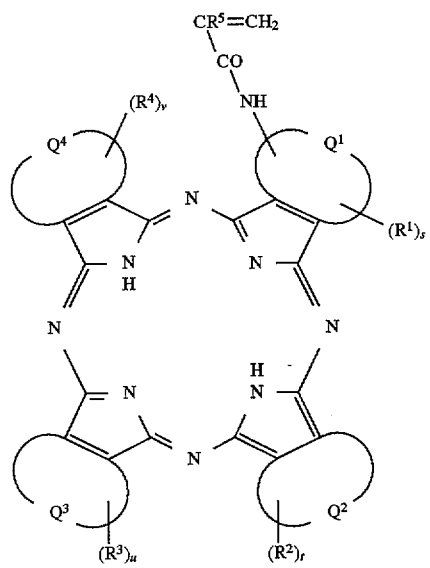

(4)

In formula (4), $Q^1$ to $Q^4$, $R^1$ to $R^4$, s, t, u and v are as defined in formula (2).

$R^5$ is a hydrogen atom or an alkyl group which may be straight or branched and substituted or unsubstituted. Alkyl groups having 1 to 4 carbon atoms are preferred. Exemplary are methyl, ethyl, propyl, and butyl groups. Most preferably $R^5$ is a hydrogen atom or methyl.

The vinyl-containing naphthalocyanine compounds of formula (4) may be those of the following formula (15):

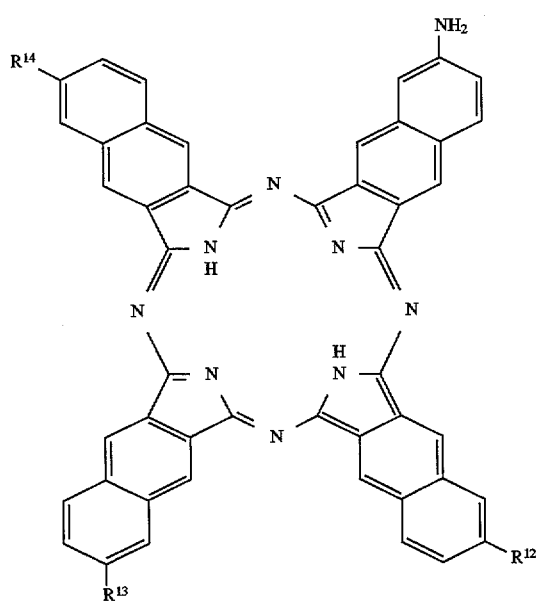

(14)

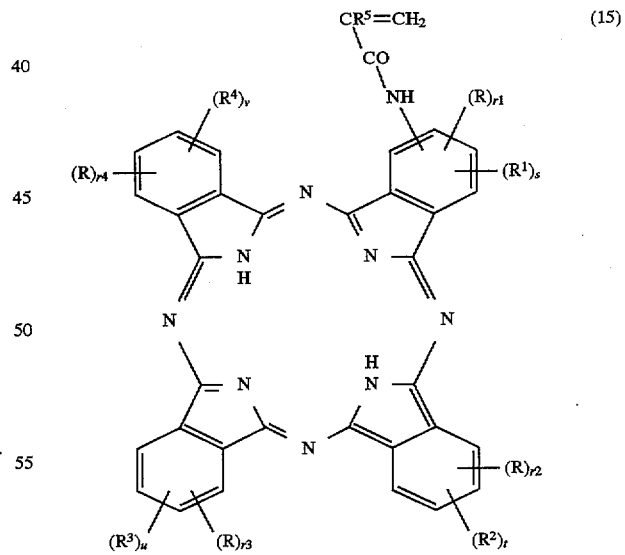

(15)

In formulae (13) and (14), $R^{12}$ to $R^{14}$ are as defined in formulae (10) and (11) both for general and preferred examples. Like formulae (10) and (11), combinations of $R^{12}$ to $R^{14}$ for formulae (13) and (14) are as shown in Table 1. The same discussion as above applies to (the choice of the four rings completed by $Q_1$ to $Q^4$ and the number of substituents.

Like the nitro-substituted naphthalocyanine compounds, the amino-substituted naphthalocyanine compounds of the invention may be metal naphthalocyanine compounds. The coordinating metal atom M is as defined previously both for general and preferred examples.

In the fourth aspect, the present invention provides vinyl-containing naphthalocyanine compounds of formula (4).

wherein R, r1 to r4, $R^1$ to $R^4$, s, t, u and v are as defined in formula (9) both for general and preferred examples.

Among the vinyl-containing naphthalocyanine compounds of formula (4), exemplary preferred compounds are represented by the following formulae (16) and (17).

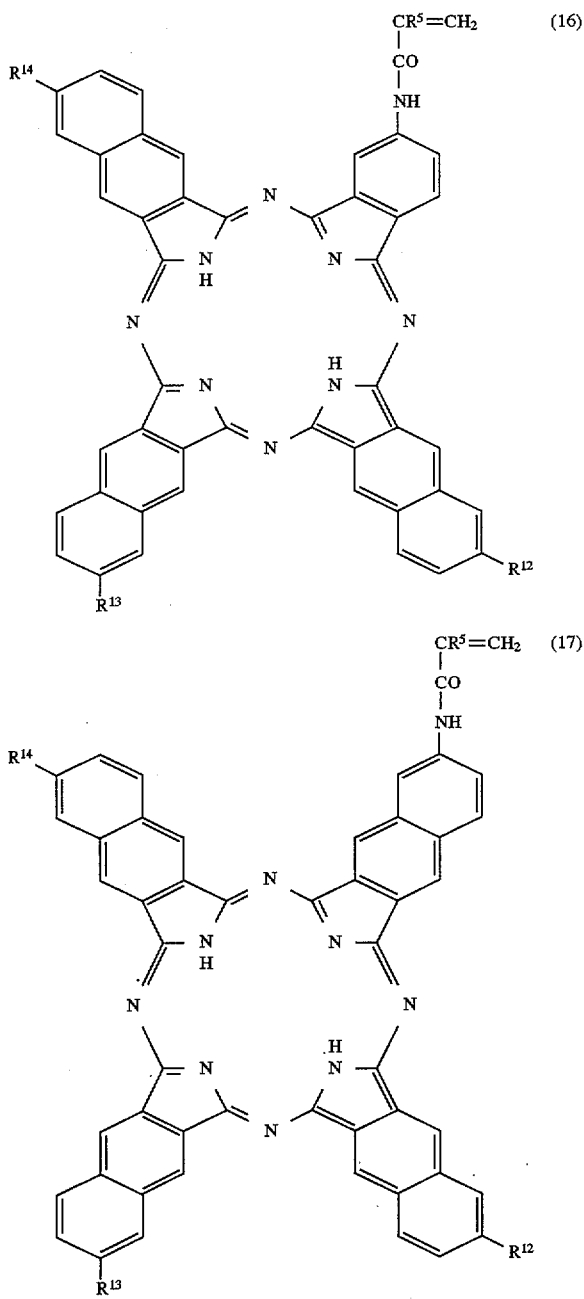

In formulae (16) and (17), $R^5$ is as defined in formula (15) and $R^{12}$ to $R^{14}$ are as defined in formulae (10) and (11), both for general and preferred examples.

Preferred illustrative examples of the vinyl-containing naphthalocyanine compounds of formula (4) are shown in Table 2 which represents combinations of $R^5$, $R^{12}$, $R^{13}$, and $R^{14}$ in formulae (16) and (17).

TABLE 2

| Compound designation | $R^5$ | $R^{12}$ | $R^{13}$ | $R^{14}$ |
|---|---|---|---|---|
| M-1 | H | $t\text{-}C_4H_9$ | $t\text{-}C_4H_9$ | $t\text{-}C_4H_9$ |
| M-2 | $CH_3$ | $t\text{-}C_4H_9$ | $t\text{-}C_4H_9$ | $t\text{-}C_4H_9$ |
| M-3 | H | $s\text{-}C_4H_9$ | $s\text{-}C_4H_9$ | $s\text{-}C_4H_9$ |
| M-4 | H | $t\text{-}C_5H_{11}$ | $t\text{-}C_5H_{11}$ | $t\text{-}C_5H_{11}$ |
| M-5 | H | $t\text{-}C_6H_{13}$ | $t\text{-}C_6H_{13}$ | $t\text{-}C_6H_{13}$ |
| M-6 | H | $i\text{-}C_3H_7$ | $i\text{-}C_3H_7$ | $i\text{-}C_3H_7$ |
| M-7 | H | $t\text{-}C_4H_9O$ | $t\text{-}C_4H_9O$ | $t\text{-}C_4H_9O$ |
| M-8 | H | $s\text{-}C_4H_9O$ | $s\text{-}C_4H_9O$ | $s\text{-}C_4H_9O$ |
| M-9 | H | $t\text{-}C_5H_{11}O$ | $t\text{-}C_5H_{11}O$ | $t\text{-}C_5H_{11}O$ |
| M-10 | H | $t\text{-}C_6H_{13}O$ | $t\text{-}C_6H_{13}O$ | $t\text{-}C_6H_{13}O$ |
| M-11 | H | $i\text{-}C_3H_7O$ | $i\text{-}C_3H_7O$ | $i\text{-}C_3H_7O$ |
| M-12 | H | $C_2F_5$ | $C_2F_5$ | $C_2F_5$ |
| M-13 | H | $t\text{-}C_4F_9$ | $t\text{-}C_4F_9$ | $t\text{-}C_4F_9$ |
| M-14 | H | $CH_3\text{-}CH(F)\text{-}CHO$ | $CH_3\text{-}CH(F)\text{-}CHO$ | $CH_3\text{-}CH(F)\text{-}CHO$ |

It is understood that the same discussion as above applies to the choice of the four rings completed by $Q^1$ to $Q^4$ and the number of substituents.

Like the foregoing naphthalocyanine compounds, the vinyl-containing naphthalocyanine compounds of the invention may be metal naphthalocyanine compounds. The coordinating metal atom M is as defined previously both for general and preferred examples.

METHOD

Described hereinafter are methods for preparing the nitro-substituted naphthalocyanine compound of formula (2), amino-substituted naphthalocyanine compound of formula (3), and vinyl-containing naphthalocyanine compound of formula (4). Since the nitro- and amino-substituted naphthalocyanine compounds of formulae (2) and (3) are available as intermediates in the preparation of the vinyl-containing naphthalocyanine compound of formula (4), the overall method for the preparation of the vinyl-containing naphthalocyanine compound of formula (4) is described in order.

First, phthalonitrile compounds (inclusive of a dicyanonaphthalene compound) corresponding to the end product are selected. More particularly, there are used at least one member selected from the group consisting of a phthalonitrile which may have a substituent $R^2$, $R^3$ or $R^4$ such as an alkyl group and a dicyanonaphthalene which may have a substituent $R^2$, $R^3$ or $R^4$ such as an alkyl group and at least one member selected from the group consisting of a nitrophthalonitrile which may have a substituent $R^1$ and a dicyanonitronaphthalene which may have a substituent $R^1$. Predetermined amounts of the phthalonitrile compounds are reacted in a non-aqueous solvent such as n-pentanol in the presence of a strong base catalyst such as 1,5-diazabicyclo[4,3,0]non-5-ene (DBN). The reaction product is purified to obtain a nitro-substituted naphthalocyanine compound of formula (2). The reaction temperature is about 70° to 110° C. and the reaction time is about 20 to about 48 hours. In general, reaction is effected under reflux.

Then, the nitro group of the nitro-substituted naphthalocyanine compound of formula (2) is reduced using a reducing agent such as $SnCl_2$ in a dispersing medium such as ethanol. The reaction product is purified to obtain an amino-substituted naphthalocyanine compound of formula (3). In general, reaction is effected at a temperature of about 25° C. for a time of about 24 hours.

Next, the amino-substituted naphthalocyanine compound of formula (3) is reacted with an acryloyl group-containing compound such as acryloyl chloride which is dependent on the end naphthalocyanine compound. The reaction product is purified to obtain a naphthalocyanine compound of formula (4) having an acryloyl group introduced therein. In general, reaction is effected in a non-aqueous solvent such as tetrahydrofuran (THF) in the presence of a base such as triethylamine. The reaction temperature is about 0° C. and the reaction time is about 2 hours.

A metal is introduced into the nitro-substituted naphthalocyanine compound of formula (2), amino-substituted naphthalocyanine compound of formula (3) or vinyl-containing naphthalocyanine compound of formula (4), for example, by mixing a 0.1M solution of a salt of the metal to be introduced (for example, an acetate, chloride, bromide, and carbonate, as well as acetylacetonatoaluminum complex or the like for aluminum to be introduced) with a 1M solution of the compound and maintaining the mixture at a temperature of about 100° C. for 24 hours for reaction, followed by purification. The reaction medium may be methanol, chloroform, pyridine, phenol or the like. Reaction is generally effected under reflux. In this way, the respective naphthalocyanine compounds are converted into corresponding compounds wherein the two hydrogen atoms are replaced by a metal.

When it is desired to produce a rather general form of compound of formula (1) wherein $M^1=2H$, the preparation of the nitro-substituted naphthalocyanine compound of formula (2) can be followed. It can be produced by selecting at least one dicyanonaphthalene which may have a substituent $R^1$, $R^2$, $R^3$ or $R^4$ and optionally, at least one phthalonitrile which may have a substituent $R^1$, $R^2$, $R^3$ or $R^4$ and reacting predetermined amounts of these compounds. When it is desired to obtain a compound of formula (1) wherein $M^1$ is a metal, a metal may be introduced into the compound of formula (1) wherein $M^1=2H$ by the same procedure as above.

These products are identifiable by infrared (IR) absorption spectroscopy, mass spectrometry, elemental analysis or visible absorption spectroscopy.

Most of the above-mentioned series of reactions are solution reactions using solvents while some use dispersion media. Since a metal-free naphthalocyanine compound having bulky alkyl groups such as t-butyl groups can be directly synthesized, the resulting compound is of high purity as compared with conventional methods including a synthesis method of reacting a metal salt with a dicyanonaphthalene to form a metal naphthalocyanine compound and a synthesis method of converting a Li naphthalocyanine into a metal-free form with the aid of HCl Followed by replacement by another metal. The purity is about 80% in the conventional methods and increased to about 95 to 100% at any stage by the inventive method. This is because the respective compounds obtained at several reaction stages are well soluble as compared with the conventional methods, allowing purification to be made at each of the reaction stages, leading to higher purity.

The naphthalocyanine compounds of formulae (1), (2), (3) and (4) according to the invention have higher solubility than prior art naphthalocyanine compounds. This is probably because the naphthalocyanine compounds of the invention are of the structure having bulky substituents such as alkyl or alkoxy groups, typically t-butyl groups attached to the benzene or naphthalene ring of the naphthalocyanine ring. More particularly, conventional phthalocyanine and naphthalocyanine compounds have the nature that their molecules tend to associate with each other and are poorly soluble because of this nature. Introduction of bulky alkyl or alkoxy groups restrains association and improves solubility.

As a result, the naphthalocyanine compounds of the invention are well soluble in solvents such as acetone and chloroform. Although conventional naphthalocyanine compounds are insoluble in such solvents, the naphthalocyanine compounds of the invention have a solubility of about 30% by weight in acetone at 25° C. and about 30 to 40% by weight in chloroform at 25° C. They have a solubility of about 2.5% to about 15% by weight in ethyl cellosolve which is often used as a solvent for dissolving a dye to form a dye coating in optical recording discs.

It is also preferable to introduce fluorinated alkyl or alkoxy groups. Fluorine substitution is effective for improving the solubility of the relevant compounds in fluorinated solvents such as fluorinated alcohols. For example, the compounds have a solubility of about 3 to 10% by weight in fluorinated solvents.

Further, those compounds having $Si(OR_1)_2$ as a center ligand have a solubility of about 5% to about 15% by weight in ethyl cellosolve which is often used as a dye dissolving solvent in the manufacture of optical recording discs.

The vinyl-containing naphthalocyanine compounds of formula (4) which may optionally have a metal introduced therein are useful monomers for forming polymers because they have a polymerizable vinyl group.

The metal naphthalocyanine compound is obtained by once synthesizing a metal-free naphthalocyanine compound and introducing a metal therein. This process enables introduction of almost all metals and a choice may be made from a wide variety of metal naphthalocyanine compounds. Any metal naphthalocyanine compound can be synthesized depending on a particular purpose and application.

The foregoing naphthalocyanine compounds of the invention have a maximum absorption wavelength λmax in the range of 550 to 850 nm. They are thus expected to find use as photo-functional materials accommodating to the wavelength of semiconductor lasers. More particularly, because of acceptable solubility, they are useful as dyes for producing optical recording media having a dye coating as a recording layer, for example, optical recording discs, typically write-once compact discs. For this application, the compounds are advantageously converted into copolymers for facilitating coating as will be described later.

The absorption characteristics of the naphthalocyanine compounds depend on the proportion of benzene ring to naphthalene ring, the type of substituent, and the like. It is especially advantageous that the absorption characteristics vary with the proportion of benzene ring to naphthalene ring. More specifically, λmax shifts to a longer wavelength as the proportion of naphthalene ring increases. Such wavelength control also applies to reflection characteristics, enabling to provide a high reflectivity at a predetermined wavelength. Any of naphthalocyanine compounds can be selected, depending on the intended purpose and application, so as to match with the wavelength of a particular laser. For use as a dye film of a write-once compact disc, for example, a compound having at least one benzene ring among the four rings is preferred from the standpoint of solubility and reflection. Wavelength control as mentioned just above can also be made by fluorine substitution. It is also expectable to use the inventive compounds as photosensitive substances.

Polymer

The naphthalocyanine polymer of the invention has a structural unit of the formula (5).

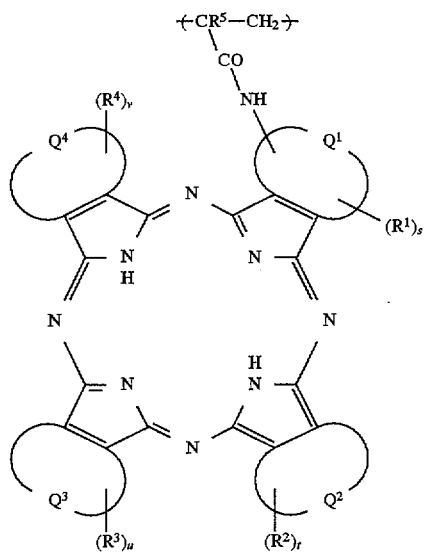

(5)

In formula (5), $Q^1$ to $Q^4$, $R^1$ to $R^5$, s, t, u, and v are as defined in formula (4). The polymer may be a homopolymer in which recurring structural units are identical or a copolymer in which recurring structural units are different. Copolymers include copolymers consisting of structural units of formula (5) wherein the structural units are different since substituents like R are different and copolymers of a structural unit of formula (5) combined with another monomeric component. The copolymers may be alternating copolymers, block copolymers or random copolymers.

The naphthalocyanine-containing polymer has a number average molecular weight of about 2,500 to 30,000 and an average degree of polymerization of about 4 to 110. The polymer has a terminal group in the form of an alkyl group such as methyl.

The structural unit of formula (5) may be one having the following formula (18):

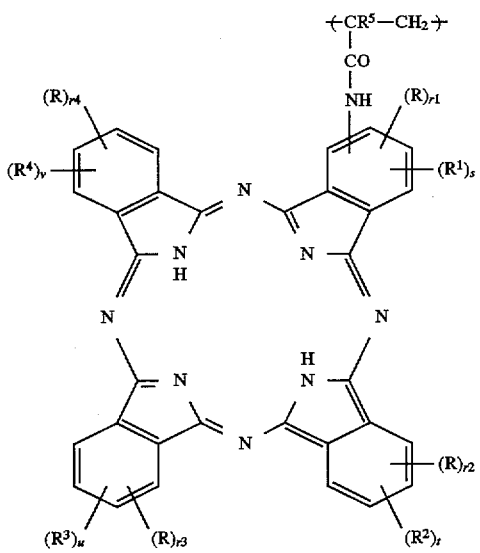

(18)

wherein $R^1$ to $R^5$, s to v, R, and r1 to r4 are as defined in formula (15). Among these naphthalocyanine series polymers, preferred examples of the copolymer consisting of structural units of formula (5) are copolymers consisting of structural units of formulae (19) and (20).

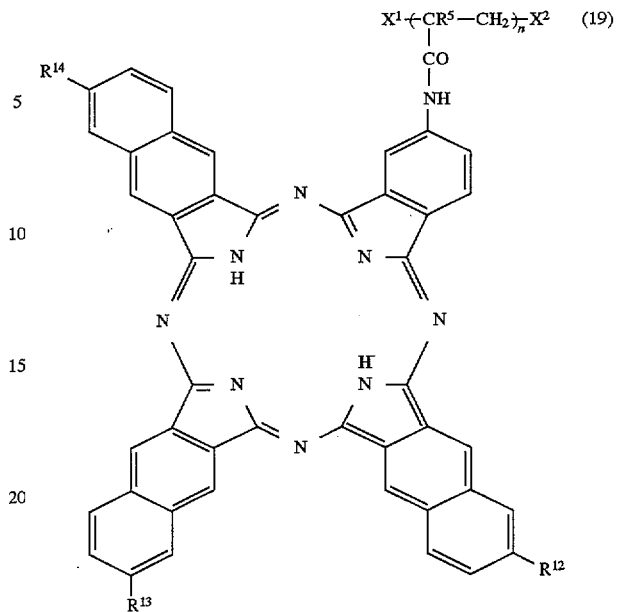

(19)

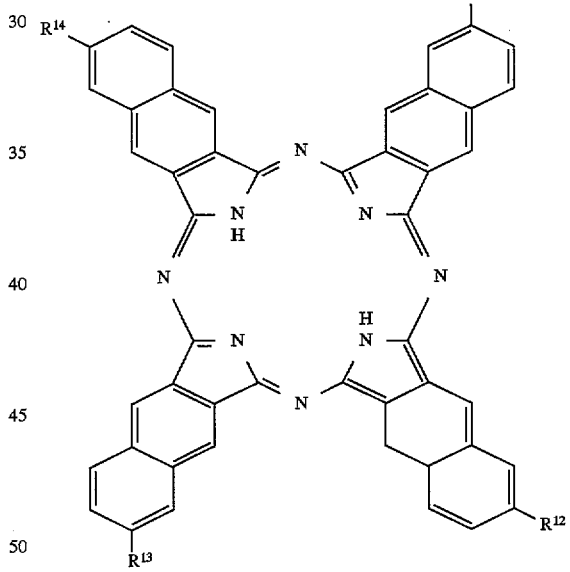

(20)

In formulae (19) and (20), $R^{12}$, $R^{13}$, $R^{14}$, and $R^5$ are as defined in formulae (16) and (17), with their preferred combinations being shown in Table 2. Letter n representative of an average degree of polymerization ranges from about 15 to about 35. $X^1$ and $X^2$ representative of a terminal group are alkyl groups such as methyl.

Generally the copolymers of formulae (19) and (20) have a number average molecular weight of about 15,000 to 30,000. Preferably the copolymers of formulae (19) and (20) are homopolymers.

Also contemplated herein are naphthalocyanine polymers having a structural unit of the general formula (6).

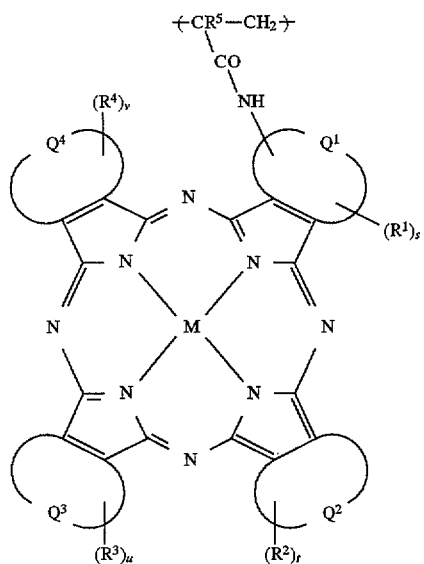

(6)

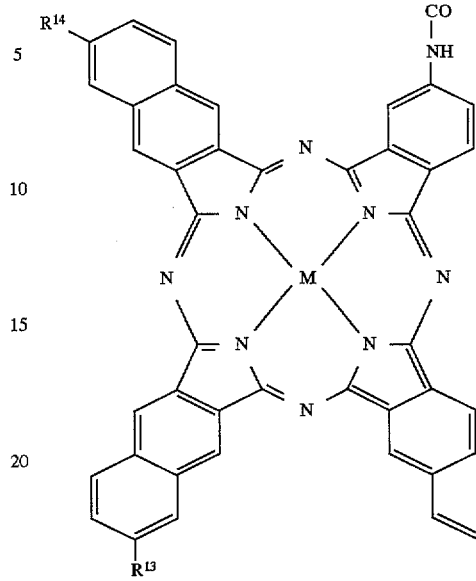

(22)

Formula (6) is the same as formula (5) except that a metal is introduced into the naphthalocyanine instead of the two hydrogen atoms. The same discussion as the polymer having structural units of formula (5) applies to the polymer having structural units of formula (6).

In formula (6), $Q^1$ to $Q^4$, $R^1$ to $R^5$, and s to v are as defined in formula (5).

The structural unit of formula (6) may be one having the following formula (21):

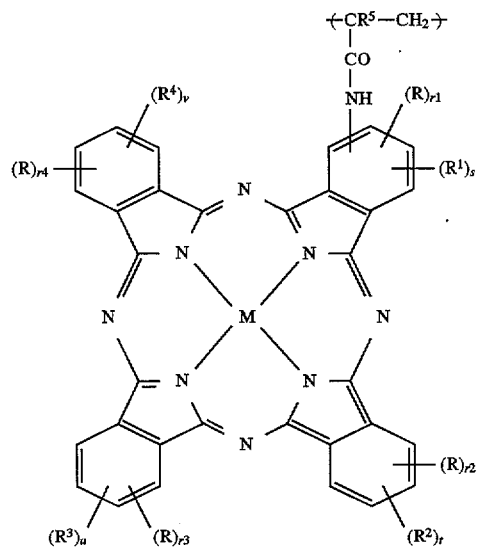

(21)

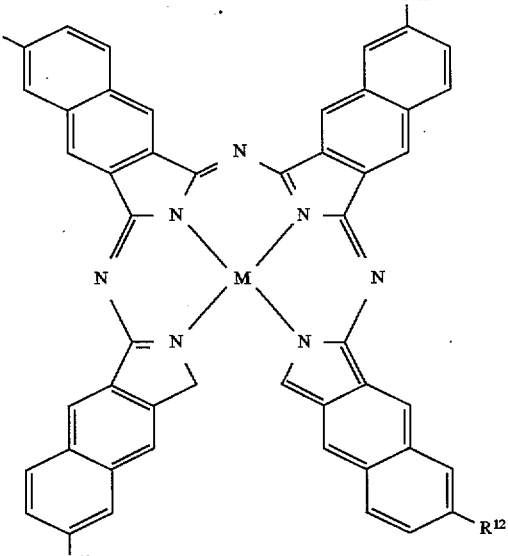

(23)

wherein $R^1$ to $R^5$, s to v, R, and r1 to r4 are as defined in formula (18) and M is as previously defined.

Preferred examples of the copolymer consisting of structural units of formula (6) are copolymers consisting of structural units of the following formulae (22) and (23).

Formulae (22) and (23) correspond to formulae (19) and (20) with a metal atom M substituting for the two hydrogen atoms. Illustrative examples are similar to the foregoing ones.

Generally the metal naphthalocyanine copolymers have a number average molecular weight of about 15,000 to 30,000 and an average degree of polymerization (n) in the range of about 15 to about 35. Terminal groups represented by $X^1$ and $X^2$ in formulae (22) and (23) are the same as above.

The inventive naphthalocyanine series copolymer is not limited to the structural units represented by formulae (5) and (6) and may contain any desired monomer component. Such other monomer components include vinyl pyridine, vinyl carbazole, styrene, N-vinylpyrrolidone, vinyl chloride, vinylidene chloride, vinyl fluoride, vinylidene fluoride, vinyl methyl ether, vinyl acetate, acrylic acid, methacrylic acid and derivatives thereof (e.g., acrylonitrile and phosphate-containing acryl monomer), maleic anhydride, and ethylene.

Water-soluble or hydrophilic examples of these copolymers are those copolymers containing acrylamide (derived from acrylic acid) or acrylamide derivative as the other monomer component. Illustrative examples of such copolymers are shown by formulae (24) and (25). These examples have a metal naphthalocyanine ring.

groups and amino-substituted alkyl groups, which both preferably have 1 to 18 carbon atoms. Exemplary alkyl groups are —$(CH_2)_3N(CH_3)_2$, —$(CH_2)_3N^+(CH_3)_3Cl^-$, and —$CH(CH_3)_2$. Letter x has a value satisfying $0<x<1$, preferably from 0.005 to 0.2. Letter n representative of an average degree of polymerization ranges from about 30 to about 100. Generally these copolymers have a number average molecular weight of about 3,000 to 20,000.

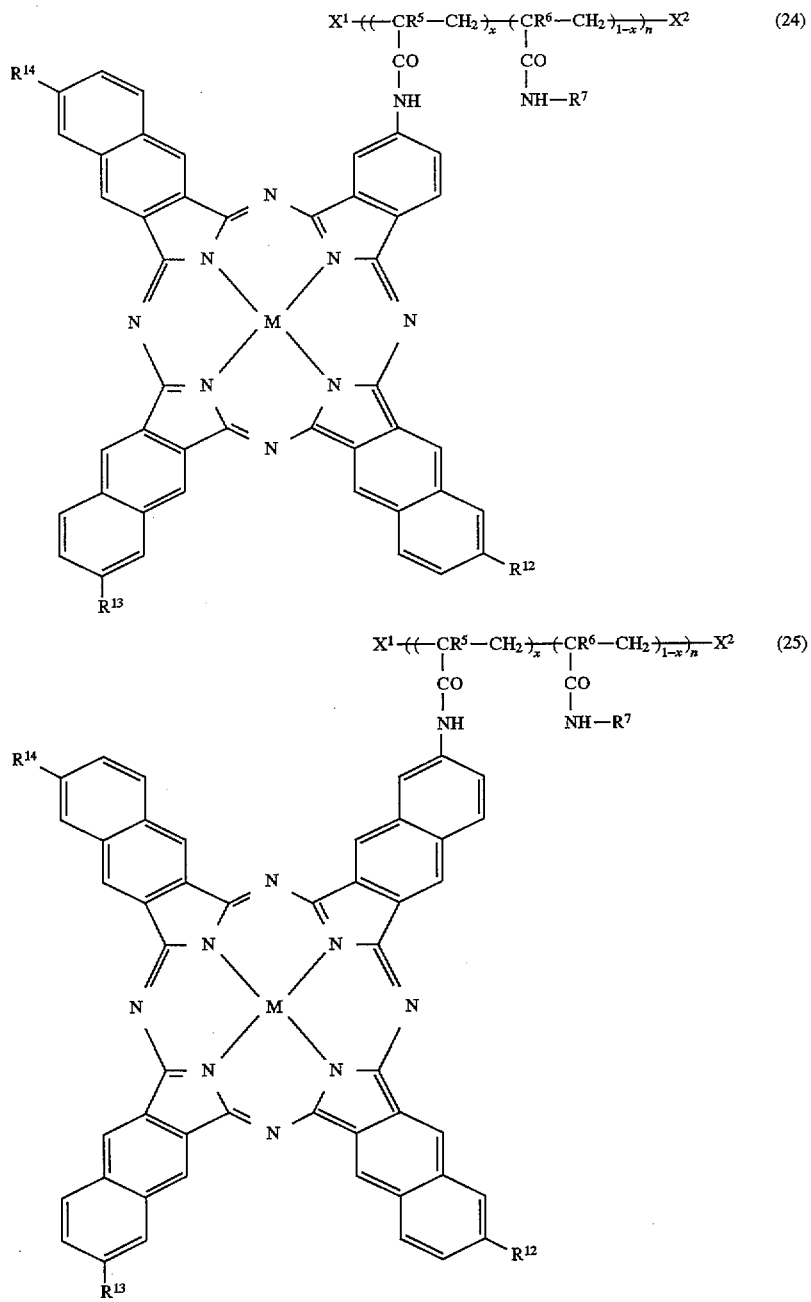

In Formulae (24) and (25), $R^5$, $R^{12}$ to $R^{14}$, $X^1$, $X^2$, and M are as defined in formulae (22) and (23). $R^6$ is a hydrogen atom or alkyl group as defined for $R^5$ in formula (4), with preferred examples being the same as $R^5$. $R^5$ and $R^6$ are generally identical though they may be different. $R^7$ is a hydrogen atom or an alkyl group. The alkyl group represented by $R^7$ is preferably selected from unsubstituted alkyl Illustrative examples of the metal naphthalocyanine copolymers of formulae (24) and (25) are those having combinations of $R^5$ to $R^7$ and $R^{12}$ to $R^{14}$ as shown in Table 3. such combinations also apply to the metal-free naphthalocyanine copolymers.

TABLE 3

| Combination No. | $R^{12}$ | $R^{13}$ | $R^{14}$ | $R^5$ | $R^6$ | $R^7$ | x |
|---|---|---|---|---|---|---|---|
| CP-1 | t-butyl | t-butyl | t-butyl | H | H | H | 0.01 |
| CP-2 | t-butyl | t-butyl | t-butyl | H | H | —(CH$_2$)$_3$N(CH$_3$)$_2$ | 0.1 |
| CP-3 | t-butyl | t-butyl | t-butyl | H | H | —(CH$_2$)$_3$N$^+$(CH$_3$)$_3$Cl— | 0.1 |
| CP-4 | t-butyl | t-butyl | t-butyl | CH$_3$ | CH$_3$ | —(CH$_2$)$_3$N(CH$_3$)$_2$ | 0.1 |
| CP-5 | t-butyl | t-butyl | t-butyl | H | H | —CH(CH$_3$)$_2$ | 0.01 |
| CP-6 | t-butoxy | t-butoxy | t-butoxy | H | H | H | 0.01 |

Illustrative examples of the naphthalocyanine copolymers further include those of formulae (26) and (27) which have a metal naphthalocyanine ring and contain N-vinylpyrrolidone as another monomer component.

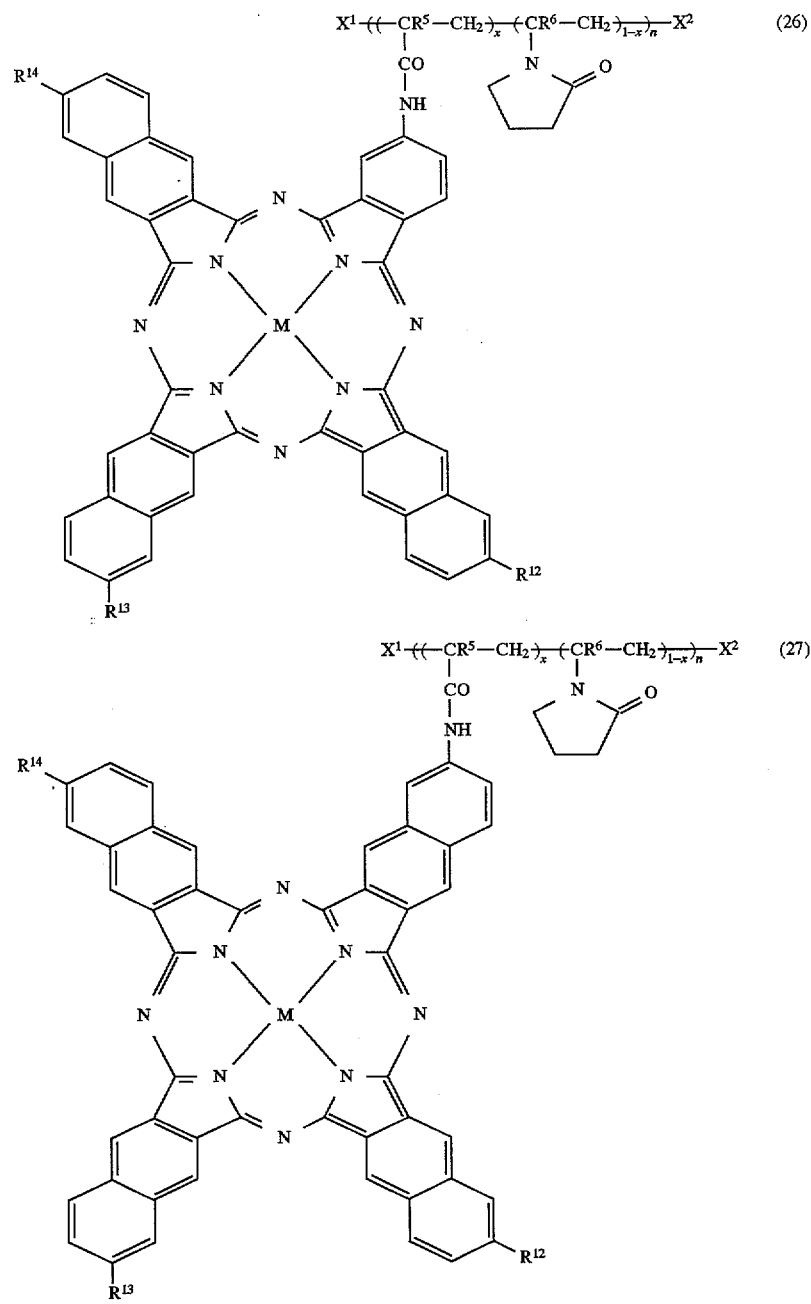

In formulae (26) and (27), $R^5$, $R^{12}$ to $R^{14}$, $X^1$, $X^2$, and M are as defined in formulae (22) and (23). $R^6$ is as defined in formulae (24) and (25). Letter x has a value satisfying $0<x<1$, preferably from 0.1 to 0.85. Letter n representative of an average degree of polymerization ranges from about 5 to about 15. Generally these copolymers have a number average molecular weight of about 3,700 to 12,000.

The copolymers of formulae (26) and (27) may be metal free.

For the remaining copolymers, the number average molecular weight, average degree of polymerization, terminal groups and the like are the same as above.

In the polymers of formulae (22) and (23) wherein M is Fe(II), pyrazine or tetrazine may coordinate with M so that some or all of M atoms are coupled through pyrazine or tetrazine. Examples of the polymer having tetrazine coordinated therewith are represented by the following formula (28).

has about 0.1 M. The reaction medium may be methanol, chloroform, pyridine, phenol or a mixture thereof with water. The reaction temperature is about 100° C. and the reaction time is about 24 hours. By such reaction, the metal atom M is introduced into about 90 to 100% by weight of the naphthalocyanine ring in the polymer.

Preferably, a metal naphthalocyanine polymer as represented by formula (6) is obtained by once synthesizing a metal-free naphthalocyanine polymer and introducing a metal atom M into the polymer. On the contrary, if a metal naphthalocyanine compound is subject to radical polymerization, radical growth is inhibited. Therefore, a polymer having a higher degree of polymerization and a higher molecular weight is obtained from the route of polymerizing a metal-free compound. As compared with the route of polymerizing a metal naphthalocyanine compound, the route of polymerizing a metal-free compound is easy to control the orientation of naphthalocyanine rings to form a

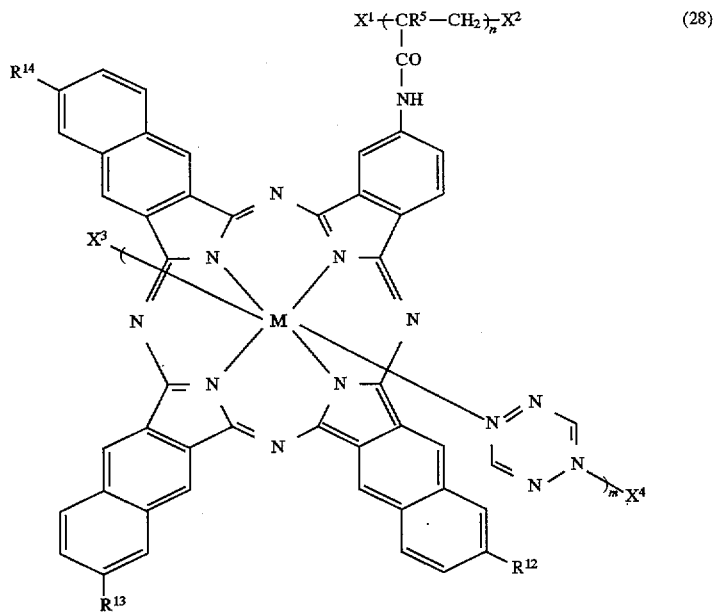

(28)

In formula (28), $R^5$, $R^{12}$ to $R^{14}$, $X^1$, $X^2$, M and n are as defined in formulae (22) and (23), $X^3$ and $X^4$ have the same meaning as $X^1$ and $X^2$, and letter m is 10 to 20.

These polymers have a number average molecular weight equivalent to those of formulae (22) and (23).

The naphthalocyanine polymer of formula (5) is prepared by polymerizing a naphthalocyanine compound of formula (4) followed by purification. Polymerization may be effected using a non-aqueous solvent such as benzene and a radical initiator such as α,α'-azobisisobutyronitrile (AIBN). The reaction temperature is about 60° C. and the reaction time is about 20 to 48 hours.

The copolymer containing another monomer component is prepared by similar reaction with a monomer component such as acrylamide, derivatives thereof, and N-vinylpyrrolidone being added.

The metal naphthalocyanine polymer as represented by formula (6) is obtained by substituting a metal atom for the two hydrogen atoms of the naphthalocyanine ring of the above-prepared polymer of formula (5). For substitution of metal atom M, a solution of a salt of the desired metal is added to a solution of the polymer followed by mixing as previously mentioned. At this point, the metal salt solution has a concentration of about 1 M and the polymer solution linear polymer because of the eliminated interaction between metal atoms. This also provides the advantage that the metal to be introduced into naphthalocyanine ring can be selected from a wider range and the content of metal naphthalocyanine ring is increased.

Nevertheless, it is possible in some cases to prepare a metal naphthalocyanine-containing polymer by polymerizing a metal naphthalocyanine compound of formula (4) (with a metal introduced). When such a route is selected, a regular arrangement of naphthalocyanine rings is expectable. Furthermore, by using a metal-free naphthalocyanine compound and a metal naphthalocyanine compound in suitable combination as starting monomers, formation of a branched polymer or a three-dimensional polymer can be promoted or suppressed such that a desired polymer may be obtained.

The naphthalocyanine-containing polymers of the invention can be identified by IR spectroscopy, mass spectrometry, elemental analysis, and visible absorption spectroscopy. The number average molecular weight and average degree of polymerization can be determined by gel permeation chromatography (GPC).

The thus obtained naphthalocyanine-containing polymers, especially metal naphthalocyanine-containing polymers have many advantages over the conventional ones including a higher content of naphthalocyanine, easy control of orientation of naphthalocyanine rings, high purity, and increased solubility.

A comparison of solubility in chloroform at 25° C. among various naphthalocyanine-containing polymers inside and outside the scope of the invention reveals that most conventional polymers have a solubility of 0% whereas the inventive polymers have a solubility of about 30 to 40% by weight, indicating increased solubility. Especially the copolymers of formulae (24) and (25) are water soluble as long as x ranges from 0.005 to 0.2 and their solubility in water at 25° C. is equivalent to that of conventional acrylamide polymers. That is, there are obtained water soluble naphthalocyanine-containing polymers. Moreover, the copolymers of formulae (26) and (27) are well soluble in various solvents such as ethyl cellosolve, diacetone alcohol, and 2,2,3,3-tetrafluoropropanol. For example, they have a solubility of about 5 to 15% by weight in ethyl cellosolve.

For these reasons, the naphthalocyanine polymers, especially metal naphthalocyanine polymers of the present invention are expected to be chemically stable functional materials which will find use in light absorption, electric conduction, photo-conduction, energy conversion, electrode and catalyst. Especially, the naphthalocyanine-containing copolymers of formulae (26) and (27) whether they are metal free or not are well soluble in solvents used in forming dye coatings in the manufacture of optical recording discs such as write-once compact discs (CD-R) and have λmax in the range of 550 to 850 nm like the aforementioned monomers. These copolymers are useful dyes in the recording layer of CD-R. Furthermore, the polymer of formula (28) may be formed into a film which serves as a conductive film when doped with iodine.

EXAMPLE

Examples or the present invention are given below by way of illustration and not by way of limitation.

Example 1

Synthesis of a nitro-substituted nadhthalocyanine compound of formula (10) wherein $R^{12}=R^{13}=R^{14}$=t-butyl group In 100 ml of n-pentanol were dissolved 4 grams ($1.71 \times 10^{-2}$ mol) of t-butyl-6,7-dicyanonaphthalene and 1 gram ($5.68 \times 10^{-3}$ mol) of nitrophthalonitrile. The solution was heated and refluxed for 24 hours in nitrogen in the presence of 10.1 grams of 1,5-diazabicyclo [4,3,0]non-5-ene (DBN) catalyst, precipitating a product. The heating temperature was about 100° C. The precipitated product was dissolved in chloroform (CHCl$_3$) and purified with silica gel, obtaining an end product designated Compound A1 in a yield of 1.5 grams (30%).

This compound was 99% pure. It was identified by elemental analysis, IR spectroscopy (KBr tablet method) and mass spectrometry, with the following results.

| Elemental analysis | | | |
|---|---|---|---|
| | C | H | N |
| Calcd. (%) | 76.60 | 5.41 | 14.42 |
| Found (%) | 76.70 | 5.52 | 14.28 |
| IR | | | |
| ν NO$_2$ | 1540 cm$^{-1}$ | | |

| -continued | |
|---|---|
| δ NO$_2$ | 1430 cm$^{-1}$ |
| Mass spectrometry | |
| m/e | 878 (M + 1) |

Other nitro-substituted naphthalocyanine compounds of formula (10) wherein the combination of $R^{12}$, $R^{13}$, and $R^{14}$ was changed as in Table 1 were similarly synthesized. These compounds were similarly identified.

These nitro-substituted naphthalocyanine compounds had a solubility of about 30% by weight in acetone at 25° C.

Example 2

In 10 ml of CHCl$_3$ was dissolved 2.5 grams ($2.87 \times 10^{-3}$ mol) of Compound A1 obtained in Example 1. To the solution was added 5 ml of a methanol solution of $2.87 \times 10^{-2}$M copper acetate. The mixed solution was heated and refluxed at 100° C. for 24 hours, obtaining a compound having copper introduced into the naphthalocyanine ring, designated Compound B1. The end of reaction was confirmed by visible absorption spectroscopy. Compound B1 was purified by recrystallizing from chloroform/n-hexane. The yield was 2.6 grams (80%). The purity was 100%.

| Elemental analysis | | | |
|---|---|---|---|
| | C | H | N |
| Calcd. (%) | 71.60 | 13.41 | 4.82 |
| Found (%) | 71.10 | 13.10 | 4.93 |
| IR | | | |
| ν NO$_2$ | 1540 cm$^{-1}$ | | |
| δ NO$_2$ | 1430 cm$^{-1}$ | | |
| Mass spectrometry | | | |
| m/e | 942 (M + 1) | | |

The synthesis of Compound B was repeated except that the copper acetate was replaced by cobalt acetate, zinc acetate, and acetylacetonatoaluminum complex, obtaining compounds having cobalt, zinc and aluminum incorporated therein, respectively. These compounds were similarly identified and had a purity equivalent to that of Compound B1.

By similarly introducing copper, cobalt, zinc, and aluminum into the compounds of Example 1 other than Compound A1 compounds similar to Compound B1 were obtained. These compounds were similarly identified and had a purity equivalent to that of Compound B1.

These compounds had a solubility of about 30% by weight in acetone at 25° C.

Example 3

Synthesis of an amino-substituted naphthalocyanine compound of formula (13) wherein $R^{12}=R^{13}=R^{14}$=t-butyl group Compound A1 obtained in Example 1, 2.5 grams ($2.87 \times 10^{-3}$ mol), was dispersed in 30 ml of a solvent mixture of ethanol and HCl (volume ratio 2/1) in an ice bath. An ethanol solution of $4.42 \times 10^{-2}$M SnCl$_2$·2H$_2$O was added dropwise to the dispersion. After 24 hours, the reaction mixture was neutralized with aqueous ammonia, precipitating a product. The precipitated product was dissolved in CHCl$_3$ and purified with active alumina, obtaining an end product designated Compound C1 in a yield of 0.6 grams (30%).

This compound was approximately 100% pure. It was identified by elemental analysis, IR spectroscopy (KBr tablet method) and mass spectrometry, with the following results.

| Elemental analysis | | | |
|---|---|---|---|
| | C | H | N |
| Calcd. (%) | 79.32 | 5.82 | 14.91 |
| Found (%) | 78.90 | 5.81 | 14.88 |
| IR | | | |
| ν NH$_2$ | 3300 cm$^{-1}$ | | |
| Mass spectrometry | | | |
| m/e | 848 (M + 1) | | |

Other amino-substituted naphthalocyanine compounds of formula (13) wherein the combination of $R^{12}$, $R^{13}$, and $R^{14}$ was changed were similarly synthesized from the other nitro-substituted naphthalocyanine compounds of Example 1. These compounds were similarly identified and had an equivalent purity.

These amino-substituted naphthalocyanine compounds had a solubility of about 30 to 40% by weight in chloroform at 25° C.

Example 4

As in Example 2, copper, cobalt, zinc and aluminum were introduced into the amino-substituted naphthalocyanine compounds of Example 3. The resulting compounds were similarly identified.

These compounds had a purity of 99% and a solubility of about 30 to 40% in chloroform at 25° C.

Example 5

Synthesis of a naphthalocyanine compound of formula (16) (combination M-1 in Table 2)

Compound C1 synthesized in Example 3, gram (1.43×10$^{-3}$ mol), was dissolved in 50 ml of tetrahydrofuran (THF) in an ice bath and reacted with 0.3 grams (3.33×10$^{-3}$ mol) of acryloyl chloride in the presence of triethylamine. After 2 hours, the THF was distilled off, obtaining a reaction product. The product was dissolved in dichloromethane and purified with active alumina. The product was further dissolved in CHCl$_3$ and methanol was added dropwise to the solution. By recrystallization an end product (Compound M-1-1) was recovered in a yield of 0.9 gram (80%). It was approximately 100% pure.

| Elemental analysis | | | |
|---|---|---|---|
| | C | H | N |
| Calcd. (%) | 78.50 | 5.71 | 14.01 |
| Found (%) | 78.42 | 5.80 | 14.20 |
| IR | | | |
| ν C=C | 1625 cm$^{-1}$ | | |
| ν C=O | 1650 cm$^{-1}$ | | |
| Mass spectrometry | | | |
| m/e | 902 (M + 1) | | |

Like Compound M-1-1, the remaining compounds in Table 2 were synthesized. They were similarly identified and had an equivalent purity.

These naphthalocyanine compounds had a solubility of about 30 to 40% by weight in chloroform at 25° C.

Example 6

As in Example 2, copper, cobalt, zinc, and aluminum were introduced into the naphthalocyanine compounds of Example 5. The resulting compounds were similarly identified.

These compounds had a purity of 99% and a solubility of about 30 to 40% in chloroform at 25° C.

Example 7

Synthesis of polymer of formula (19) wherein $R^{12}=R^{13}=R^{14}=$t-butyl group, $R^5$=H, $X^1=X^2=CH_3$ To a benzene solution of 0.5 M Compound M-1-1 of Example 5, AIBN was added in an amount of 2% by weight. The solution was heated and refluxed for 24 hours. The heating temperature was 60° C. After polymerization reaction, an end product designated Polymer P-1-1 was purified by re-precipitation. The yield was 1 gram (30%).

The polymer was approximately 100% pure and had a number average molecular weight of 20,000 to 30,000 and an average degree of polymerization (n) of 25 to 35.

| Elemental analysis | | | |
|---|---|---|---|
| | C | H | N |
| Calcd. (%) | 78.58 | 5.72 | 14.01 |
| Found (%) | 78.60 | 5.74 | 14.00 |
| IR | | | |
| ν C=O | 1650 cm$^{-1}$ | | |

Like Compound M-1-1, the remaining compounds in Table 1 were used as a starting monomer and similarly polymerized to produce polymers. The polymers were similarly identified. The polymers had the same terminal groups as mentioned above. The polymers had a number average molecular weight of 20,000 to 30,000 and an average degree of polymerization of 25 to 35.

The polymers had a solubility of 30 to 40% by weight in chloroform at 25° C. The purity was of the same order as above.

Example 8

To a chloroform solution of 2.87×10$^{-3}$ M Polymer P-1-1 synthesized in Example 7, a methanol solution of 2.87×10$^{-3}$ M zinc acetate was added. The solution was heated and refluxed for 24 hours at a temperature of 100° C. There was obtained a polymer having zinc incorporated into the naphthalocyanine ring, designated Polymer PM-1-1. It was purified as in Example 7. The yield was 1 gram (80%).

The end of reaction was confirmed by visible absorption spectroscopy as in Example 2. Polymer PM-1-1 had a metal substitution of about 97% by weight. It was approximately 100% pure and had a number average molecular weight of 20,000 to 30,000 and an average degree of polymerization of 25 to 35. The terminal group was the same as in Example 7.

| Elemental analysis | | | |
|---|---|---|---|
| | C | H | N |
| Calcd. (%) | 71.40 | 4.83 | 13.44 |
| Found (%) | 70.93 | 4.90 | 13.41 |
| IR | | | |
| ν C=O | 1650 cm$^{-1}$ | | |

Polymers were prepared by the same procedure as Polymer PM-1-1 except that zinc was replaced by copper, cobalt and aluminum as in the foregoing Examples. These polymers were similarly identified.

Similarly, copper, cobalt, zinc, and aluminum were introduced into the polymers of Example 7 other than Polymer P-1-1, obtaining polymers similar to Polymer PM-1-1. They were similarly identified.

With respect to purity, metal substitution, and terminal group, these polymers were the same as Polymer PM-1-1. They had a number average molecular weight of 20,000 to 30,000 and an average degree of polymerization of 25 to 35.

The polymers had a solubility of 30 to 40% by weight in chloroform at 25° C.

Example 9

Synthesis of copolymer of formula (24) (combination CP-1 in Table 3, M=2H, $X^1=X^2=CH_3$)

A benzene solution of 0.5M Compound M-1-1 synthesized in Example 5 was mixed with a dimethylformamide (DMF) solution of 0.01M $CH_2=CH-CO-NH_2$. AIBN was added to the solution in an amount of 2% by weight. The solution was heated and refluxed at 60° C. for 24 hours, obtaining an end product designated CP-1-1. It was purified by repeating dialysis and filtration. The yield was 1.5 grams (92%).

The copolymer was approximately 100% pure and had a number average molecular weight of 3,000 to 20,000 and an average degree of polymerization (n) of 30 to 100. The results of elemental analysis were well coincident with the calculated values. The solubility of the copolymer in water at 25° C. was as high as acrylamide polymers.

In addition to the above copolymer, a corresponding copolymer having Co introduced therein, and metal-free and metal-introduced copolymers of formula (24) having the remaining combinations shown in Table 3 were synthesized. They were similarly identified. With respect to purity, number average molecular weight, average degree of polymerization, and solubility, these copolymers were the same as Copolymer CP-1-1.

Example 10

The procedure of Example 1 was repeated except that 4 grams ($1.71 \times 10^{-3}$ mol) of t-butyl-6,7-dicyanonaphthalene and 1.27 grams ($5.68 \times 10^{-3}$ mol) of 6,7-dicyanonitronaphthalene were used as the starting reactants. There was obtained a nitro-substituted naphthalocyanine compound A2 of formula (11) wherein $R^{12}=R^{13}=R^{14}$=t-butyl group. The yield was 1.5 grams (32%).

The compound has a purity of 100% and a solubility equivalent to the compound of Example 1. It was identified as in Example 1.

Example 11

Using Compound A2 of Example 10, a compound having copper introduced therein, B2, was prepared as in Example 2. The yield was 0.8 gram (90%).

The compound has a purity of 100% and a solubility equivalent to the compound of Example 2. It was identified as in Example 2.

Example 12

Using Compound A2 of Example 10, an amino-substituted naphthalocyanine compound C2 of formula (14) wherein $R^{12}=R^{13}=R_{14}=R^{14}$=t-butyl group was prepared as in Example 3. The yield was 0.5 gram (30%).

The compound has a purity of 100% and a solubility equivalent to the compound of Example 3. It was identified as in Example 3.

Example 13

Using Compound C2 of Example 12, a compound having copper introduced therein, D2, was prepared as in Example 2. The yield was 0.8 gram (82%).

The compound has a purity of 100% and a solubility equivalent to the compound of Example 4. It was identified as in Example 4.

Example 14

Using Compound C2 of Example 12, a naphthalocyanine compound M-1-2 of formula (17) having combination M-1 in Table 2 was prepared as in Example 5. The yield was 1.0 gram (90%).

The compound has a purity of 100% and a solubility equivalent to the compound of Example 5. It was identified as in Example 5.

Example 15

Using Compound M-1-2 of Example 14, a polymer P-1-2 of formula (20) wherein $R^{12}=R^{13}=R^{14}$=-butyl group, $R^5$=H, $X^1=X^2=CH_3$ was prepared as in Example 7. The yield was 0.3 gram (32%).

The polymer was 100% pure and had a number average molecular weight, average number of polymerization (n) and solubility equivalent to the polymer of Example 7. It was identified as in Example 7.

Example 16

Using Polymer P-1-2 of Example 15, a polymer having zinc introduced therein, PM-1-2, was prepared as in Example 8. The yield was 0.3 gram (00%).

The polymer was 97% pure and had a metal substitution, number average molecular weights, average number of polymerization (n) and solubility equivalent to the polymer of Example 8. It was identified as in Example 8.

Example 17

Synthesis of naphthalocyanine compound of formula (8) wherein $R^{11}=R^{12}=R^{13}=R^{14}$=t-$C_4H_9-$, $M^1$=2H In 100 ml of n-pentanol were dissolved 1.0 gram ($4.30 \times 10^{-3}$ mol) of t-butyl-6,7-dicyanonaphthalene and 2.4 grams (1.29×10⁻² mol) of t-butylphthalonitrile. The solution was heated and refluxed for 24 hours in nitrogen in the presence of 10.1 grams of 1,5-diazabicyclo [4,3,0]non-5-ene (DBN) catalyst, precipitating a product. The heating temperature was about 100° C. The precipitated product was dissolved in chloroform (CHCl₃) and purified with silica gel, obtaining an end product designated Compound A3 in a yield of 1.2 grams (40%).

This compound was 97% pure. It was identified by elemental analysis, IR spectroscopy (KBr tablet method) and mass spectrometry, with the following results.

| Elemental analysis | | | |
|---|---|---|---|
| | C | H | N |
| Calcd. (%) | 79.39 | 6.36 | 14.24 |
| Found (%) | 78.62 | 6.41 | 14.30 |

| IR | |
|---|---|
| ν $CH_2$ | 2850 cm⁻¹ |
| Mass spectrometry | |
| m/e | 674 (M + 1) |

This naphthalocyanine compound had a solubility of about 30% by weight in acetone at 25° C. and λmax of 680 nm.

Example 18

Synthesis of naphthalocyanine compound of formula (8) wherein $R^{11}=R^{12}=R^{13}=R^{14}=OCH(F)(CH_3)$, $M^1=Si(OC_2H_5)_2$ In 100 ml of n-pentanol were dissolved 0.96 gram (4.30×10⁻³ mol) of mono fluorinated ethoxy-6,7-dicyanonaphthalene and 2.33 grams (1.34×10⁻² mol) of monofluorinated ethoxyphthalonitrile. The solution was heated and refluxed for 24 hours in nitrogen in the presence of 10.1 grams of 1,5-diazabicyclo[4,3,0]non-5-ene (DBN) catalyst, precipitating a product. The heating temperature was about 100° C. The precipitated product was dissolved in chloroform (CHCl3) and purified with silica gel, obtaining a product designated Compound A4.

The resulting Compound A4 of formula (8) wherein $M^1=2H$, 1 gram, was reacted with 0.8 gram of $SiCl_4$ in pyridine while heating them under reflux, obtaining a compound having $SiCl_2$ at the center. The compound was hydrolyzed in an aqueous solution of $NH_4OH$, obtaining a compound having $Si(OH)_2$ at the center. The compound was heated and refluxed in ethanol, obtaining an end product designated Compound B4. It was purified as in Example 2. The yield was 1.20 grams (30%).

This compound was 95% pure. It was identified by elemental analysis, IR spectroscopy (KBr tablet method) and mass spectrometry, with the following results.

| Elemental analysis | | | |
|---|---|---|---|
| | C | H | N |
| Calcd. (%) | 70.78 | 4.02 | 12.87 |
| Found (%) | 71.01 | 4.10 | 12.70 |

| -continued | |
|---|---|
| IR | |
| ν $CH_2$ | 2850 cm⁻¹ |
| Mass spectrometry | |
| m/e | 746 (M + 1) |

This naphthalocyanine compound had a solubility of about 30% by weight in acetone at 25° C. and λmax of 690 nm.

Example 19

In 50 ml of THF were dissolved 4 mol of Compound M-1-1 synthesized in Example 5 and 1 mol of N-vinylpyrrolidone. AIBN was added as a polymerization catalyst in an amount of 2% by weight. The solution was heated and refluxed for 4 hours, obtaining a vinylnaphthalocyanine-vinylpyrrolidone copolymer of formula (26) wherein $R^5=R^6=H$, $R^{12}=R^{13}=R^{14}=$t-butyl, $X^1=X^2=CH_3$.

The copolymer had a number average molecular weight of 3,700 to 12,000 and an average degree of polymerization (n) of 5 to 15. The ratio of structural units, vinylnaphthalocyanine/vinylpyrrolidone was 4/1, that is, x =0.8 in formula (26). It was well soluble in various solvents. For example, it had a solubility of 10% by weight in ethyl cellosolve. The purity was 98%. The results of elemental analysis were well coincident with the calculated values. The yield was 2 grams (80%). λmax was 750 nm.

Example 20

Synthesis of polymer P-1-1 in Example 8 was repeated except that $FeBr_2$ was used, obtaining a polymer of formula (22) wherein the center metal was Fe(II).

This polymer, 1 gram (1.05×10⁻³ mol), was dissolved in 10 ml of chloroform and 0.2 gram (3.20×10⁻³ mol) of tetrazine was added to the solution. The solution was heated and refluxed for two days. After two days, the resulting polymer was re-precipitated from n-hexane and dried, obtaining a polymer of formula (28) wherein $R^5=H$, $R^{12}=R^{13}=R^{14}=$t-butyl group, $X^1=X^2CH_3$, M=FE(II).

The polymer had a number average molecular weight of 20,000 and an average degree of polymerization (n) of 20. In formula (28), m was 10 to 20. It had a solubility of 10% by weight in acetone and a purity of 98%. The results of elemental analysis were well coincident with the calculated values. The yield was 0.0 gram (75%). The absorption spectrum exhibited a λmax of 790 nm.

Example 21

The copolymer of formula (26) synthesized in Example 19 was dissolved in ethyl cellosolve to form a coating solution of 10% by weight. A polycarbonate resin substrate of 120 mm in diameter and 1.2 mm thick was coated with the coating solution by spin coating, forming a recording layer containing the dye. On the recording layer, a reflecting layer and then a protective layer were overlaid, obtaining an optical recording disc (CD-R). The recording layer was 150 nm thick (dry film thickness). The reflecting layer was formed by sputtering Au to a thickness of 85 nm. The protective layer was formed from a UV curable acrylic resin to a thickness of 5 μm.

Signals were recorded in this optical recording disc. Recording was possible with a laser power of 7 mW at a wavelength of 780 nm. Read-out with a laser at a wavelength of 780 nm revealed a reflectivity (Itop) of 70% and a modulation of 65%, clearing the Orange Book Standard.

The disc was kept under conditions: 60° C. and RH 90% for five days before it was examined by the same write/read test, finding no substantial deterioration.

Example 22

An optical recording disc was fabricated by the same procedure as Example 21 except that the recording layer was formed by coating a 3% by weight ethyl cellosolve solution of Compound A3 synthesized in Example 17. The disc was examined by the same write/read test as in Example 21, obtaining at least equivalent results.

Example 23

An optical recording disc was fabricated by the same procedure as Example 21 except that the recording layer was formed by coating a 2.5% by weight diacetone alcohol solution of Compound B4 synthesized in Example 18. The disc was examined by the same write/read test as in Example 21, obtaining at least equivalent results.

Example 24

On an aluminum-deposited substrate, 18 grams of the nitro-substituted naphthalocyanine compound B5 of Example 2 which was obtained by introducing aluminum into Compound A1 of Example 1 and which is represented by formula (10) wherein $R^{12}=R^{13}=R^{14}$=t-butyl group and Al instead of 2H, was evaporated under a vacuum of $2\times10^{-6}$ Torr and deposited to a thickness of about 500 A. On the naphthalocyanine compound layer deposited on the aluminum-deposited substrate, a solution containing 10 parts by weight of 1-phenyl-3-(p-diethylaminostyryl)-5-(p-diethylaminophenyl) pyrazolone and 10 parts by weight of a phenoxy resin in 150 parts by weight of THF was spin coated. The coating was dried at 100° C. for one minute to form an electric charge transfer layer having a dry thickness of 15 μm. The resulting photosensitive laminate was charged negative by an electric discharge at 6 kV. Light decay of its surface potential was measured using a 500-W Xe lamp as a light source and a monochrometer for monochromatic light measurement. The inverse of the light quantity (μJ/cm²) necessary to reduce the surface potential to one half of the initial was evaluated as sensitivity.

The results are shown in FIG. 1, which shows that a high sensitivity of 1.3 to 1.8 cm²/μJ is available over the range of 650 to 800 nm.

Example 25

A solution of the polymer of formula (28) synthesized in Example 20 in acetone was cast to form films of 10 μm thick. Some films were doped with iodine. The doped and undoped films were measured for electric conductivity. The iodine doped films had a conductivity of $1.2\times10^{-1}$ Scm$^{-1}$ whereas the undoped films had a conductivity of 0.02 Scm$^{-1}$.

This indicates that iodine doping allows for the use of a naphthalocyanine polymer film as a conductive film.

There have been described novel naphthalocyanine compounds having improved solubility and high purity and expected to find use as photo-functional materials such as dyes and photosensitive substances, which include nitro-substituted naphthalocyanine compounds and amino-substituted naphthalocyanine compounds as well as vinyl-containing naphthalocyanine compounds synthesized therefrom. Novel polymers are obtained by using as starting monomers vinyl-containing naphthalocyanine compounds containing a polymerizable vinyl group within their molecule. The polymers can be metal naphthalocyanine polymers which have a high content of metal naphthalocyanine rings and are easy to control the orientation of naphthalocyanine rings. The control of orientation of naphthalocyanine rings is further facilitated by forming a thin film. The polymers are well soluble and some are water soluble. Their purity is high. The inventive polymers are further expected to find use as various functional materials for light absorption, electric conduction, energy conversion, electrode, catalyst and the like.

Japanese Patent Application No. 287483/1993 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for preparing a naphthalocyanine compound of the following general formula (1):

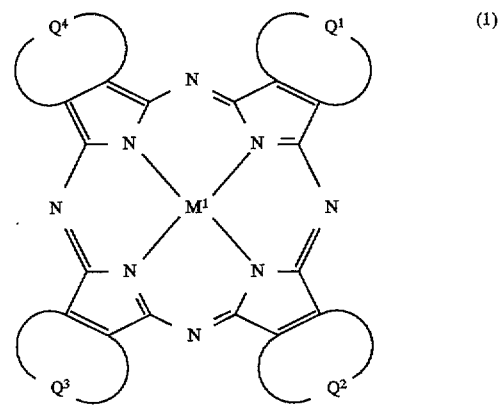

wherein each of $Q^1$, $Q^2$, $Q^3$ and $Q^4$ is a group of atoms to form a substituted or unsubstituted benzene ring or naphthalene ring fused to the adjacent pyrrole ring, at least one of the rings formed by $Q^1$, $Q^2$, $Q^3$ and $Q^4$ being a substituted or unsubstituted naphthalene ring, letter q is 0 or an integer of 1 to 4 when $Q^1$ forms a benzene ring, or 0 or an integer of 1 to 6 when $Q^1$ forms a naphthalene ring, $M^1$ is a center atom, comprising the step of reacting a phthalonitrile compound system including at least one dicyanonaphthalene and optionally at least one phthalonitrile.

2. A method for preparing a naphthalocyanine compound comprising the steps of:

reacting a phthalonitrile compound system including at least one of a substituted or unsubstituted phthalonitrile and a substituted or unsubstituted dicyanonaphthalene and at least one of a substituted or unsubstituted nitrophthalonitrile and a substituted or unsubstituted dicyanonitronaphthalene, thereby forming a nitro-substituted naphthalocyanine compound of the following general formula (2):

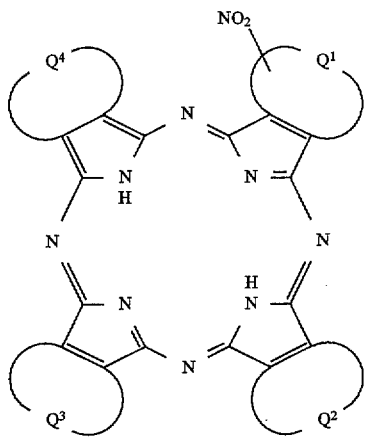

(2)

wherein each of $Q^1$, $Q^2$, $Q^3$ and $Q^4$ is a group of atoms to form a substituted or unsubstituted benzene ring or naphthalene ring fused to the adjacent pyrrole ring, at least one of the rings formed by $Q^1$, $Q^2$, $Q^3$ and $Q^4$ being a naphthalene ring, reducing the nitro group of said nitro-substituted naphthalocyanine compound into an amino-substituted naphthalocyanine compound of the following general formula (3):

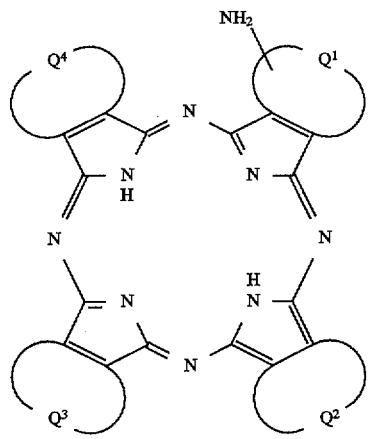

(3)

wherein each of $Q^1$, $Q^2$, $Q^3$ and $Q^4$ is a group of atoms to form a substituted or unsubstituted benzene ring or naphthalene ring fused to the adjacent pyrrole ring, at least one of the rings formed by $Q^1$, $Q^2$, $Q^3$ and $Q^4$ being a substituted or unsubstituted naphthalene ring, and introducing an acryloyl group into the amino group of said amino-substituted naphthalocyanine compound to form a naphthalocyanine compound of the following general formula (4):

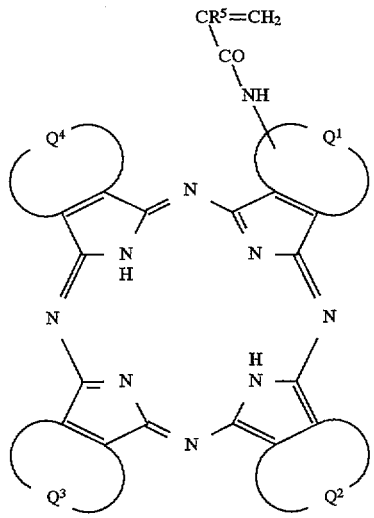

(4)

wherein each of $Q^1$, $Q^2$, $Q^3$ and $Q^4$ is a group of atoms to form a benzene ring or naphthalene ring fused to the adjacent pyrrole ring, at least one of the rings formed by $Q^1$, $Q^2$, $Q^3$ and $Q^4$ being a naphthalene ring, and $R^5$ is a hydrogen atom or an alkyl group.

3. A method for preparing a naphthalocyanine polymer comprising the step of polymerizing a naphthalocyanine compound of the following general formula (4):

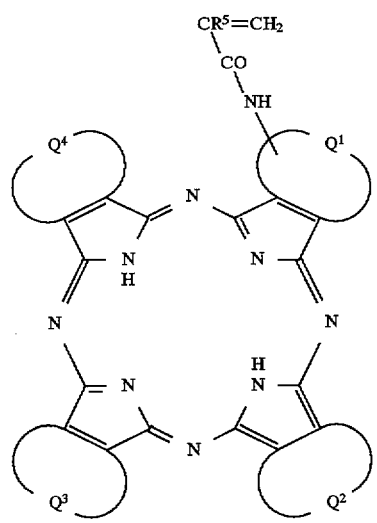

(4)

wherein each of $Q^1$, $Q^2$, $Q^3$ and $Q^4$ is a group of atoms to form a benzene ring or naphthalene ring fused to the adjacent pyrrole ring, at least one of the rings formed by $Q^1$, $Q^2$, $Q^3$ and $Q^4$ being a naphthalene ring, and $R^5$ is a hydrogen atom or an alkyl group, to form a naphthalocyanine polymer having a structural unit of the following general formula (5):

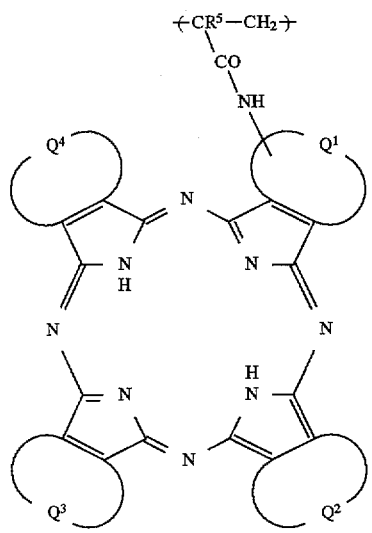 (5)

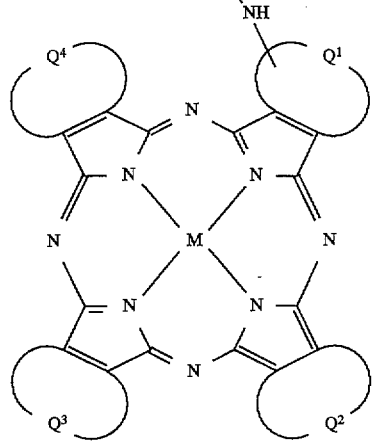 (6)

wherein each of $Q^1$, $Q^2$, $Q^3$ and $Q^4$ is a group of atoms to form a substituted or unsubstituted benzene ring or naphthalene ring fused to the adjacent pyrrole ring, at least one of the rings formed by $Q^1$, $Q^2$, $Q^3$ and $Q^4$ being a substituted or unsubstituted naphthalene ring, and $R^5$ is a hydrogen atom or an alkyl group.

4. A method for preparing a naphthalocyanine compound comprising the step of substituting a metal for the two hydrogen atoms positioned centrally of the naphthalocyanine ring of a naphthalocyanine polymer having a structural unit of the following general formula (6):

wherein each of $Q^1$, $Q^2$, $Q^3$ and $Q^4$ is a group of atoms to form a substituted or unsubstituted benzene ring or naphthalene ring fused to the adjacent pyrrole ring, at least one of the rings formed by $Q^1$, $Q^2$, $Q^3$ and $Q^4$ being a substituted or unsubstituted naphthalene ring, $R^5$ is a hydrogen atom or an alkyl group, and M is a metal atom.

* * * * *